United States Patent
Josse et al.

(10) Patent No.: US 10,801,995 B2
(45) Date of Patent: Oct. 13, 2020

(54) SHEAR HORIZONTAL-SURFACE ACOUSTIC WAVE SYSTEM AND METHOD FOR MEASUREMENT AND SPECIAION SPECIATION OF HYDROCARBONS IN GROUNDWATER

(71) Applicants: Marquette University, Milwaukee, WI (US); Chevron U.S.A. Inc., San Ramon, CA (US)

(72) Inventors: Fabien J. Josse, Brookfield, WI (US); Florian Bender, Milwaukee, WI (US); Antonio J. Ricco, Milwaukee, WI (US); Rachel Ellen Mohler, San Ramon, CA (US); Ravindra Vasant Kolhatkar, San Ramon, CA (US)

(73) Assignees: Marquette University, Milwaukee, WI (US); Chevron U.S.A. Inc., San Ramon, CA (US)

( * ) Notice: Subject to any disclaimer, the term of this patent is extended or adjusted under 35 U.S.C. 154(b) by 107 days.

(21) Appl. No.: 15/564,368

(22) PCT Filed: Jun. 13, 2016

(86) PCT No.: PCT/US2016/037221
§ 371 (c)(1),
(2) Date: Oct. 4, 2017

(87) PCT Pub. No.: WO2017/003670
PCT Pub. Date: Jan. 5, 2017

(65) Prior Publication Data
US 2018/0128781 A1 May 10, 2018

Related U.S. Application Data

(60) Provisional application No. 62/187,902, filed on Jul. 2, 2015.

(51) Int. Cl.
G01N 29/02 (2006.01)
G01N 33/18 (2006.01)
(Continued)

(52) U.S. Cl.
CPC ......... *G01N 29/022* (2013.01); *G01N 29/036* (2013.01); *G01N 29/222* (2013.01);
(Continued)

(58) Field of Classification Search
CPC ............. G01N 29/022; G01N 29/4472; G01N 29/4418; G01N 29/222; G01N 29/036;
(Continued)

(56) References Cited

U.S. PATENT DOCUMENTS 4,895,017 A 1/1990 Pyke et al.
6,237,397 B1 5/2001 Shinar et al.
(Continued)

FOREIGN PATENT DOCUMENTS

JP H06503648 4/1994
JP 2004-522561 7/2004
(Continued)

OTHER PUBLICATIONS

Wenzel, Michael J. et al. "Online drift compensation for chemical sensors using estimation theory." IEEE Sensors J. (2011) 11 225-232. (Year: 2010).*
(Continued)

*Primary Examiner* — Christopher Adam Hixson
(74) *Attorney, Agent, or Firm* — Andrus Intellectual Property Law, LLP

(57) ABSTRACT

An exemplary embodiment of a method of detecting hydrocarbons in Systems and methods for sensing analytes in an aqueous solution, include pretreating a water sample to provide a test sample. A flow cell includes at least one sensor with a polymer coating having at least partial selectivity for at least one analyte. The flow cell receives a test sample and a reference sample. At least one output signal from the at least one sensor is processed with a microcontroller using a model of the sensor response and a bank of Kalman filters to estimate a concentration of at least one analyte in the aqueous solution.

19 Claims, 9 Drawing Sheets

(51) Int. Cl.
*G01N 29/44* (2006.01)
*G01N 29/036* (2006.01)
*G01N 29/22* (2006.01)

(52) U.S. Cl.
CPC ..... *G01N 29/4418* (2013.01); *G01N 29/4472* (2013.01); *G01N 33/1833* (2013.01); *G01N 2291/014* (2013.01); *G01N 2291/02491* (2013.01); *G01N 2291/0423* (2013.01)

(58) Field of Classification Search
CPC ....... G01N 33/1833; G01N 2291/0423; G01N 2291/02491; G01N 2291/014
See application file for complete search history.

(56) References Cited

U.S. PATENT DOCUMENTS

| | | | |
|---|---|---|---|
| 6,357,278 | B1 | 3/2002 | Sivavec et al. |
| 7,568,377 | B2 | 8/2009 | Bhethanabotla et al. |
| 9,244,051 | B2 | 1/2016 | Josse et al. |
| 2003/0008407 | A1 | 1/2003 | Fu |
| 2008/0156100 | A1* | 7/2008 | Hines .................. G01N 29/022 73/584 |
| 2008/0289397 | A1 | 11/2008 | Hassan et al. |
| 2014/0011285 | A1 | 1/2014 | Josse et al. |

FOREIGN PATENT DOCUMENTS

| | | |
|---|---|---|
| JP | 2009-521682 | 6/2009 |
| JP | 2013-533489 | 8/2013 |
| RU | 66057 U1 | 8/2007 |
| SU | 1629840 A1 | 2/1991 |

OTHER PUBLICATIONS

Bender et al., "Quantification of Benzene in Groundwater Using SH-Surface Acoustic Wave Sensors", The 14th International Meeting on Chemical Sens., 2012: pp. 473-476.

Bender et al., "Analysis of Binary Mixtures of Aqueous Aromatic Hydrocarbons with Low-Phase-Noise Shear-Horizontal Surface Acoustic Wave Sensors Using Multielectrode Transducer Designs" Analytical Chemistry, vol. 86, 2014: pp. 11464-11471.

Bender et al., "Identification and Quantification of Aqueous Aromatic Hydrocarbons Using SH-Surface Acoustic Wave Sensors", Analytical Chemistry vol. 86, 2014: pp. 1794-1799.

Bender et al., Influence of Ambient Parameters on the Response of Polymer-Coated SH-Surface Acoustic Wave Sensors to Aromatic Analytes in Liquid-Phase Detection, Joint Conference of the IEEE International Frequency Control & the European Frequency & Time Form, 2011.

Bender et al. (Jul. 2013). Design of SH-Surface Acoustic Wave Sensors for Detection of ppb Concentrations of BTEX in Water, Joint UFFC, EFTF and PFM Symposium, Prague, Czech Republic.

Jones et al., "ATR-FTIR Spectroscopic Analysis of Sorption of Aqueous Analytes Into Polymer Coatings Used with Guided SH-SAW Sensors". IEEE Sensors Journal, vol. 5, No. 6, 2005: pp. 1175-1184.

Lewis et al., "A Micro-GC Based Chemical Analysis System". Defiant technologies, www.defiant-tech.com.

Li et al., "Analysis of Liquid-Phase Chemical Detection Using Guided Shear Horizontal-Surface Acoustic Wave Sensors". Analytical Chemical, vol. 77, No. 14, 2005: pp. 4595-4603.

International Search Report and Written Opinion for PCT/US2016/037221 dated Sep. 15, 2016.

International Preliminary Report on Patentability for PCT/US2016/037221 dated Jan. 2, 2018.

Zhang et al. (Jul. 2013). Resonant Characteristics of Rectangular Hammerhead Microcantilevers Vibrating Laterally in Viscous Liquid Media, Joint UFFC, EFTF and PFM Symposium, Prague, Czech Republic.

Newman et al. (Jul. 2013). Analysis of the Detection of Organophosphate Pesticides in Aqueous Solutions Using Polymer-Coated SH-SAW Sensor Arrays, Joint UFFC, EFTF and PFM Symposium, Prague, Czech Republic.

H.W. Sorenson, "Least-squares estimation from Guass to Kalman", The 14th International Meeting on Chemical Sens., 2012: pp. 473-476.

Extended European Search Report Issued in corresponding EP 16818441.4, dated Nov. 26, 2018.

Office Action for Japanese Patent Application No. 2017-566816, dated Jul. 27, 2020.

* cited by examiner

SHEAR HORIZONTAL-SURFACE ACOUSTIC WAVE SYSTEM AND METHOD FOR MEASUREMENT AND SPECIAION SPECIATION OF HYDROCARBONS IN GROUNDWATER

CROSS REFERENCE TO RELATED APPLICATION

This application is the U.S. national stage application of International Application PCT/US2016/037221, filed Jun. 13, 2016, which international application was published on Jan. 5, 2017, as International Publication WO2017/003670 in the English language. The international application is incorporated herein by reference, in entirety. The international application claims priority to U.S. Provisional Patent Application Ser. No. 62/187,902 filed Jul. 2, 2015, which is herein incorporated in entirety.

BACKGROUND

The present disclosure is related to the field of hydrocarbon sensors. More specifically, the present disclosure is related to a shear horizontal-surface acoustic wave ("SH-SAW") system for the detection of hydrocarbons in an aqueous environment.

Underground storage tanks ("USTs") for fuel and oil are commonly used, and from time to time may be prone to unintended leakage. Nearly 600,000 federally regulated USTs exist in the United States, and approximately 6,000 leaks are recorded annually as reported by the U.S. Environmental Protection Agency. As such, it is desirable to detect and monitor groundwater in situ in the vicinity of USTs.

Typically gas phase sensors are used to determine benzene concentrations at low levels. Existing practice to monitor USTs for leaks into water requires personnel to manually collect the samples from the sites, which can be costly, and send them to another location for off-site gas phase analysis. Moreover, the integrity of the collected sample can be easily compromised during collection, sample sterilization, transportation, storage, and analysis, an overall process that often spans multiple days or weeks. In short, the current monitoring method is time consuming, labor intensive, and costly, rendering the continuous or frequent monitoring of USTs highly impractical.

Detection of organic compounds can be performed using various sensor technologies, including acoustic-wave, optical and resistive technologies. However, previous solutions were able to detect some relevant analytes at the required concentration levels, but often had limits of detection insufficient to detect benzene at the appropriate levels. One solution to inadequate limits of detection is to pre-concentrate the samples prior to testing. Pre-concentration solutions are challenging to implement because the preconcentration medium or device must be heated to release the pre-concentrated sample; aqueous phases do not permit excessive heating.

A need clearly exists to develop an in-situ sensor system that is more accurate, rapid, and comparatively inexpensive for long-term monitoring of groundwater: improved management of hydrocarbon-impacted sites will require frequent analysis to provide better documentation of temporal changes in concentrations, from which spatial concentration changes can sometimes also be inferred. Such a system would also enhance and improve the real-time assessment of the efficacy of remediation measures. The sensor system should be capable of identifying and quantifying at least some organic compounds present in groundwater near USTs.

Of the many compounds present in gasoline, benzene, toluene, ethylbenzene and xylenes ("BTEX") are of particular concern due to their relatively high solubilities in water. Also, among the BTEX compounds, benzene has the lowest polymer/water partition coefficients due to having the highest water solubility, a factor that renders its detection more challenging for some detection approaches.

The task of identifying and quantifying aromatic hydrocarbons such as the BTEX compounds, particularly benzene, is challenging, not only because of the low relevant concentrations, but also due to the chemical similarity of these compounds as a group, as well as the presence of other similar aromatic compounds in groundwater. One particular complicating factor is that the number of chemical isomers increases as the numbers of carbon atoms and substituent locations around the aromatic ring increase. For example, within the substituted-benzene family, toluene is the only seven-carbon isomer, but ethylbenzene and the three xylenes are all eight-carbon chemical isomers. Due to their fairly similar physico-chemical properties, and depending as well on the nature of the sensor used, the isomers often exhibit about the same sensitivity and response time. Additional interferents may also be present in groundwater, including dissolved salts, particles and sediments, humic acid, dissolved gases, aliphatic hydrocarbons, ethers, esters, etc.

BRIEF DISCLOSURE

A sensor system is presented herein that makes use of an array of shear-horizontal surface acoustic wave ("SH-SAW") devices, coated with partially selective polymers and matched with customized signal processing based on estimation theory, in order to detect and quantify hydrocarbon compounds (e.g. BTEX compounds) in the presence of interferents typically found in groundwater.

The presently disclosed approach to on-site BTEX monitoring is to use a sensor array in which each sensor has a different, partially chemically selective coating. When the sensors, coatings, and operating parameters are properly designed and selected in such a system, the overall array response to a particular analyte is unique. Analyte identification can be made by combining both time-transient and signal-amplitude data for each element of the array—with estimation theory in order to detect and quantify BTEX compounds with greater reliability, improved chemical selectivity (even in the presence of interferents), higher quantitative accuracy, shorter time to collect the response data (using methods that do not require equilibrium to be attained before reporting a result), and shorter data processing time.

In one exemplary embodiment, analyte detection and quantification can be achieved in near-real time using estimation theory, particularly using a bank of Kalman filters or extended Kalman filters (EKF). Analytical modeling of the sensor responses in the relevant concentration range enables use of estimation theory solutions with relatively few assumptions.

An exemplary embodiment of a system for sensing hydrocarbons in an aqueous solution includes a pretreatment stage. The pretreatment stage includes a particulate filter. The pretreatment stage receives the aqueous solution to be tested and operates to provide a test sample. A flow cell includes at least one sensor with a polymer coating having at least partial selectivity for at least one analyte. The flow cell is connected to the pre-conditioning stage and receives the processed sample and a reference sample. A phase detector receives an output signal of the at least one sensor and a phase reference signal. The phase detector outputs a phase shift. The phase shift is correlated to a corresponding frequency shift. A microcontroller receives the phase shift and or frequency shift. The microcontroller executes computer readable code stored in a storage device communicatively connected to the microcontroller and processes the frequency shift with a bank of Kalman filters to estimate a concentration of at least one analyte in the aqueous solution.

An exemplary embodiment of a method of detecting hydrocarbons in an aqueous solution includes pretreating a water sample to produce a test sample by at least particle filtering the water sample. A reference sample is provided to a flow cell. The flow cell includes at least one sensor with a polymer coating having at least partial selectivity for at least one analyte. A first output signal of the sensor is measured to establish a baseline result. The test sample is provided to the flow cell. A second output signal of the sensor is measured. The baseline result is compared to the second output signal with at least a phase detector to produce a frequency shift. A sensor response to at least one analyte sought to be identified in the water sample is modeled. An initial estimate of at least one analyte concentration is produced based upon at least the modeled sensor response and the frequency shift. A refined estimate of at least one analyte concentration is produced by processing the initial estimate with a bank of Kalman filters.

DETAILED DISCLOSURE

Presently disclosed herein is a sensor system suitable for direct groundwater monitoring and capable of aqueous-phase measurement of aromatic hydrocarbons even at low concentrations (at or below 100 parts per billion (ppb)). Exemplary embodiments of the system disclosed herein are designed to speciate and quantify benzene, toluene, and ethylbenzene/xylenes (BTEX) in the presence of potential interferents. Exemplary embodiments of the system make use of polymer-coated shear-horizontal surface acoustic wave devices and a signal processing method based on estimation theory, specifically a bank of Kalman filters (KF) or extended Kalman filters (EKFs). This approach permits estimation of BTEX concentrations even from noisy data, well before the sensor response reaches equilibrium. As described in further detail herein, to utilize estimation theory, an analytical model for the sensor response to step-changes, starting from clean water, to the water sample under measurement (mixtures of multiple analytes) is formulated that makes use of both equilibrium frequency shifts and response times (for an individual analyte), the latter being specific for each combination of coated device and analyte. The model is then transformed into state-space form, and the bank of EKFs is used to estimate BTEX concentrations in the presence of interferents from transient responses prior to attainment of equilibrium.

In testing, samples contained multiple chemically similar analytes with concentrations of individual BTEX compounds in the range of 10-2000 ppb. The estimated BTEX concentrations were compared to independent gas chromatography measurements and found to be in very good agreement (within about 5-10% accuracy), even when the sample contained multiple interferents such as larger aromatic compounds or aliphatic hydrocarbons.

Figure 1:
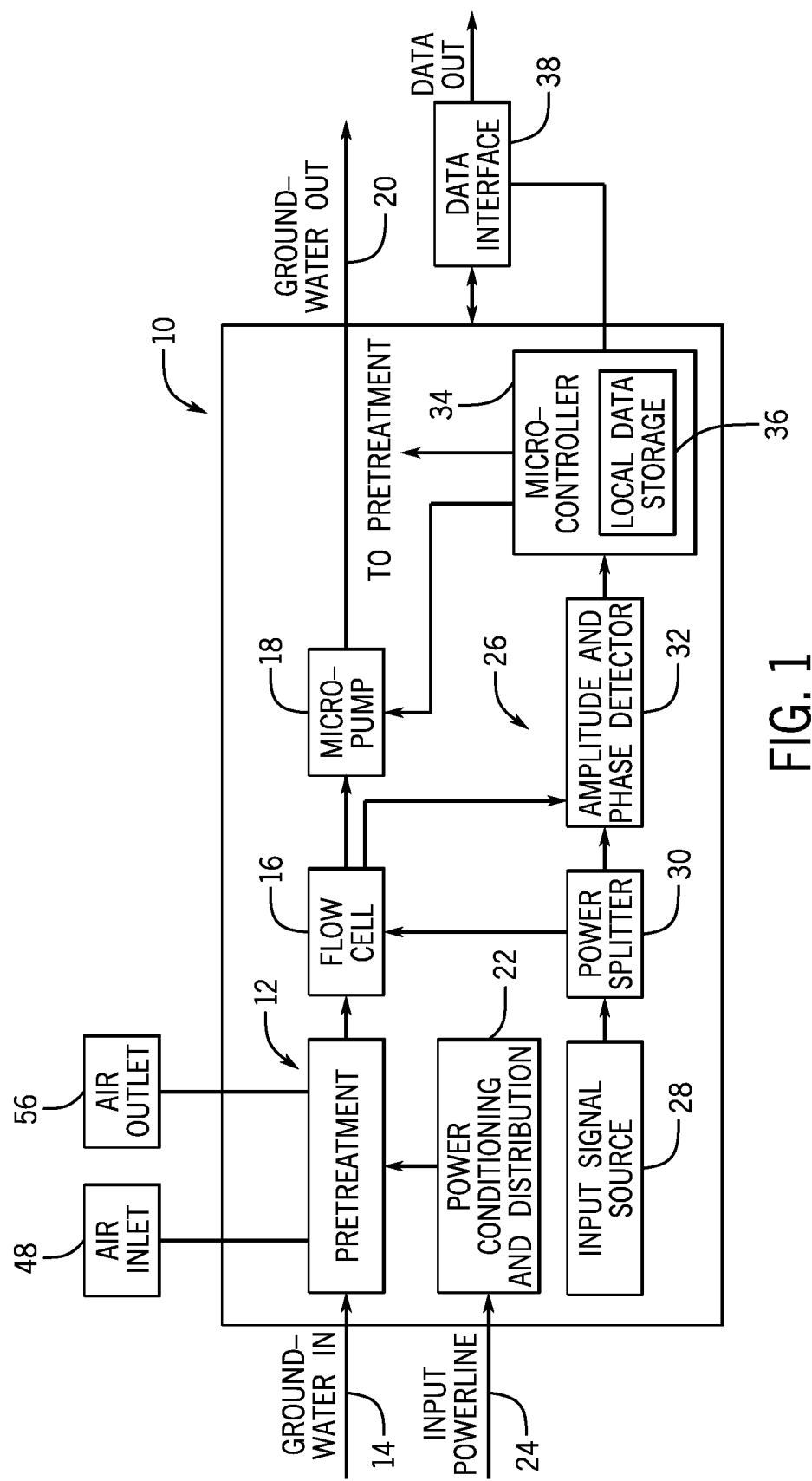
FIG. 1 is a system diagram of an exemplary embodiment of a sensor system for hydrocarbon detection and quantification.

FIG. 1 is a system diagram that depicts an exemplary embodiment of a sensor system 10 for hydrocarbon detection and quantification from an aqueous solution. The system 10 includes a pretreatment stage 12 that will be described in further detail herein. The pretreatment stage receives the aqueous fluid to be tested, exemplarily sample inlet groundwater 14. In an exemplary use, the sensor system 10 is placed in an on-water test well, including but not limited to a groundwater monitoring well located in the vicinity of one or more underground storage tanks (USTS) used for the storage of refined or unrefined hydrocarbons, for example gasoline.

After the pretreatment of the groundwater to be tested, the output samples from the pretreatment stage 12 are provided to a flow cell 16. The flow cell 16 will be described in further detail herein, particularly with respect to FIGS. 3 and 4. The flow cell 16 includes a plurality of sensors, which may include acoustic wave-based sensors, and more particularly, shear-horizontal surface acoustic wave ("SH-SAW") sensors.

A micro-pump 18 directs the tested groundwater samples out of the sensor system 10 and back into the groundwater source 20.

A sensor measurement system 26 is connected to the flow cell 16 and measures the changes in the sensor signals, received from sensors in the flow cell, as described in further detail herein. In an exemplary embodiment, the sensor measurement system 26 measures a transient frequency and amplitude response when a sensor and a flow cell 16 are exposed to groundwater samples as described herein. In exemplary embodiments, some or all of the electrical connections in the sensor measurement system 26 may be wireless connections. In still other embodiments some or all of the electrical connections in the sensor measurement system 26 may be wired connections.

The sensor measurement system 26, as will be described in further detail herein, includes an input signal source 28. The input signal source 28 provides an input signal, which is exemplarily a 102-MHz input signal. The input signal may exemplarily be provided by an RF signal generator or may be a crystal-referenced signal source. In one embodiment, an RF generator may be located remotely from the sensor system 10, in which case the input signal source 28 may be an antenna to wirelessly receive the RF signal, or may be a wired connection to the RF generator. The RF generator may exemplarily be a processor executing computer readable code to operate as an RF signal generator. In another embodiment, the input signal source 28 is a crystal-referenced source which may be electronically connected to the input power line 24 and/or the power conditioning and distribution circuit 22. The input signal source 28 provides the input signal to a power splitter 30, which operates to direct the input signal to both the flow cell 16 for use as the input signal to the flow cell 16 as described in further detail herein, as well as to provide the input signal for amplitude and frequency shift detection. While an embodiment may measure frequency directly, in an exemplary embodiment, this is carried out at least in part using a phase detector and/or an amplitude and phase detector 32. Phase shift is mathematically correlated to frequency shift, and as explained herein frequency shift may be used for mathematical modeling of the sensor responses. However, it has been observed that in some embodiments of aqueous phase measurements, phase shift detection may produce desirable frequency shift measurement results over direct measurement of frequency shift.

The amplitude and phase detector 32 receives the output of the flow cell 16 with a resulting amplitude and/or phase shift. The respective amplitude and/or phase shifts are detected by the amplitude and phase detector 32 by comparing the output signal of the flow cell 16 to the reference signal provided by the power splitter 30. The amplitude and phase detector 32 provides the differential amplitude and phase shift to a microcontroller 34. The microcontroller may convert the phase shift to a corresponding frequency shift. In another embodiment, the phase shift is converted to a corresponding frequency shift before it is provided to the microcontroller 34. The microcontroller 34 exemplarily stores measured sensor signal at the local data storage unit 36 as described in further detail herein and executes software to carry out the signal processing as described in further detail herein. The signal processing may include deriving a frequency shift that corresponds to a received phase shift. The signal processing further includes the use of at least one bank of Kalman filters to process a frequency shift in the sensor signals. In one exemplary embodiment, two banks of Kalman filters are used, a first bank of Kalman filters to provide an initial estimate of the concentration(s) of the hydrocarbon analyte(s) and a second bank of Kalman filters is used to refine the first estimate. In another exemplary embodiment, a recursive least squares technique is used as a preprocessor to narrow down the expected range of concentration(s) of the hydrocarbon analytes and a bank of Kalman filters is used to provide a refined estimate of the hydrocarbon analyte concentrations in the tested sample.

The micro controller 34 is further communicatively connected to the pretreatment system 12 and the micropump 18. More specifically the microcontroller is communicatively connected to the various valves, micropumps, and relays in the sensor system 10 to coordinate operation of the sensor by selectively providing the reference sample and the test sample to the flow cell 16 and to further purge the flow cell 16 after a testing cycle.

The microcontroller 34 is further connected to a data interface 38 of the sensor system 10, the data interface 38 may exemplarily be a wired or wireless data interface capable of transferring the processed signals and/or the estimated concentrations from the microcontroller 34 to a user. The user may exemplarily be a technician using the sensor system 10 to analyze groundwater to detect the presence of hydrocarbons in the groundwater. The data interface 38 may exemplarily include a graphical display that presents the processed signals and/or the estimated concentrations to the user.

Figure 2:
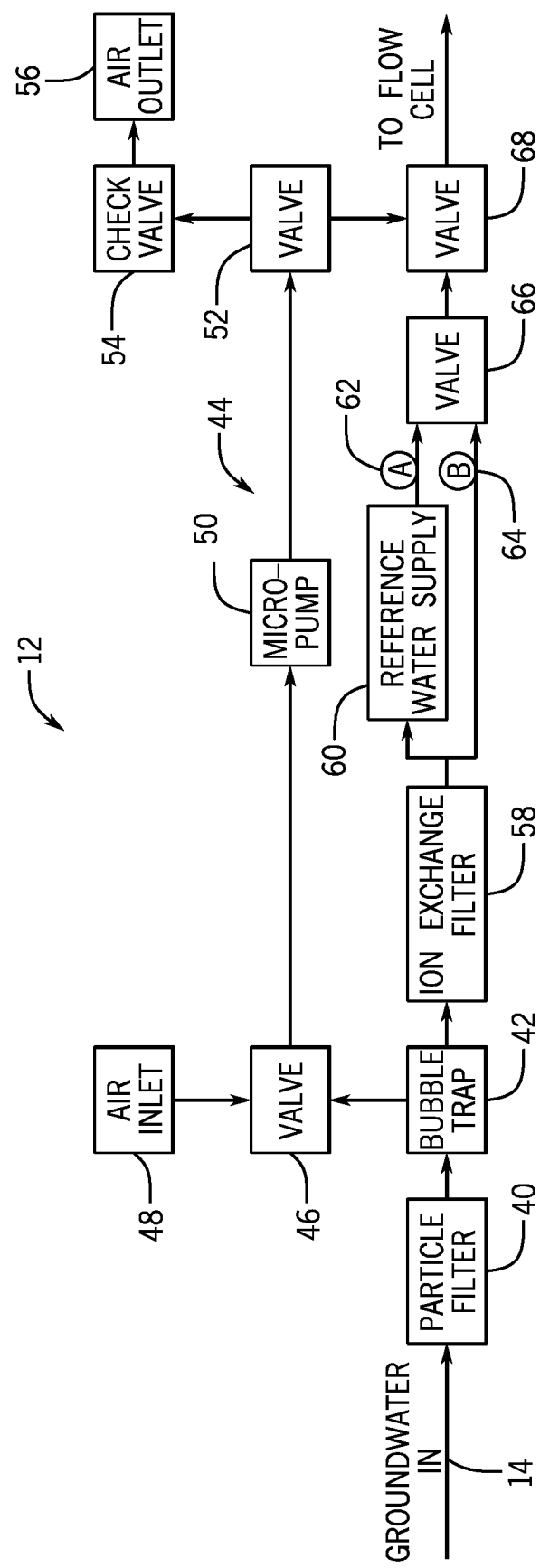
FIG. 2 is a system diagram presenting a detailed exemplary embodiment of a pretreatment stage for use with the sensor system of FIG. 1.

FIG. 2 depicts an exemplary embodiment of the pretreatment stage 12 of the sensor system described above with respect to FIG. 1. The pretreatment stage 12 receives the groundwater from the groundwater inlet 14. The groundwater sample is provided to a particle filter 40. The particle filter 40 is exemplarily a 0.2 micrometer particle filter. While a single particle filter 40 is depicted in FIG. 2, it will be understood that in the embodiment multiple particle filters may be used, for example, with decreasing pore size to improve the efficiency of the smaller pored filters. Because the presence or formation of gas bubbles in the flow cell might negatively affect the accuracy of the sensor measurement, the pretreatment stage 12 may also contain a bubble trap 42 that removes and prevents formation of gas bubbles in the water samples. Since it is the purpose of the sensor system to detect hydrocarbons such as the BTEX compounds, a bubble trap must be selected that does not impact the concentration of BTEX by removing BTEX along with the gas. Exemplarily, a 2.5 mL active debubbler (available from IDEX Health & Science, Oak Harbor, Wash.) may be used as the bubble trap 42.

The bubble trap 42 is connected to a vent 44 which exemplarily includes a valve 46 which is exemplarily a three-way valve connected between the bubble trap 42, an air inlet 48, and a micro-pump 50. The micro-pump 50 is further connected to a valve 52, which is also exemplarily a three-way valve as described in further detail herein. The valve 52 may be connected through a check valve 54 to an air outlet 56 so that the micro-pump 50 in the vent 44 is operable to vent the bubble trap 42 into the exterior of the sensor system 10. A check valve 54 may be added as a safety mechanism to prevent liquid (e.g. groundwater) or air from entering through the air outlet 56 into the system.

The sample from the bubble trap 42 is provided to an ion exchange filter 58. The ion exchange filter has the purpose to prevent formation of precipitates in the flow cell 16 or other critical parts of the system. As an example, the ion exchange filter 58 may be selected to remove humic acid and other hydrogen bond forming species from the sample. In an exemplary embodiment, the ion exchange filter 58 may be a Dionex OnGuard IIP ion exchange filter (available from Thermal Fischer Scientific, Waltham, Mass.).

Next, a reference water supply 60 provides the reference solution "A" 62. As will be explained herein, the sensor outputs from analyzing the reference solution "A" will be configured to the sensor outputs for analyzing the sample solution "B" 64. The sample solution "B" 64 may be provided from the ion exchange filter 58. In one embodiment, the reference water supply 60 may be a source of deionized (DI) water. Such a source of deionized water would require a reservoir of DI water to be provided in the sensor system 10. In the embodiment depicted in FIG. 2, the sensor system 10 produces its own reference solution "A" by further processing the sample water from the ion exchange filter 58. In such an embodiment the reference water supply 60 may further include a degassing system capable of removing petroleum hydrocarbons (which by design remain from the selected bubble trap and ion exchange filters described above). Additionally or alternatively, the reference water supply may use a filter capable of removing the petroleum hydrocarbon to produce the reference sample "A"; in an exemplary embodiment, this filter may be an activated charcoal filter. One possible advantage of producing the reference sample "A" with the reference water supply from the water sample is that any remaining impurities in the reference sample "A" after processing are similarly present in the testing sample "B" thereby providing a more representative reference that differs only in the removal of the hydrocarbon sought to be identified. The reference sample "A" and the testing sample "B" are connected to a valve 66, which is exemplarily a three-way valve and further connected to an additional valve 68. The valve 68 may further be a three-way valve connected to the vent system 44. The valve 66 operates to switch between reference sample "A" and the test sample "B" to provide to the flow cell 16 as described in further detail herein. The valve 68 operates to provide the samples to the flow cell 16 or to connect the vent system 44 to the flow cell. When the vent system 44 is connected to the flow cell through the valve 68, the micro-pump 50 can operate to direct air from the air inlet 48 through valves 52 and 68 to purge the flow cell 16 with air after the measurement. It has been discovered that this can lead to improved lifespan of the flow cell 16, particularly the polymer coatings of the sensors in the flow cell 16 as described in further detail herein.

In an additional exemplary embodiment of the pretreatment stage 12, the reference water supply 60 may further be provided with a recycling loop that connects the sample outlet 20 back to the reference water supply 60 to selectively redirect the reference sample back to the reference water supply 60 for reuse after it has flowed through the flow cell 16. In an exemplary embodiment, the recycling system may only recycle a portion of the reference sample used, for example allowing an initial portion of the reference sample to exit the same outlet and ending the recycling before any potential for contamination of the reference sample by the test samples. In still further embodiments, for example wherein the reference sample is DI water provided from a separate reservoir of water (not depicted), the reference water supply 60 may be independent from the pretreatment stage 12 and connected directly to the flow cell 16.

Figure 3:
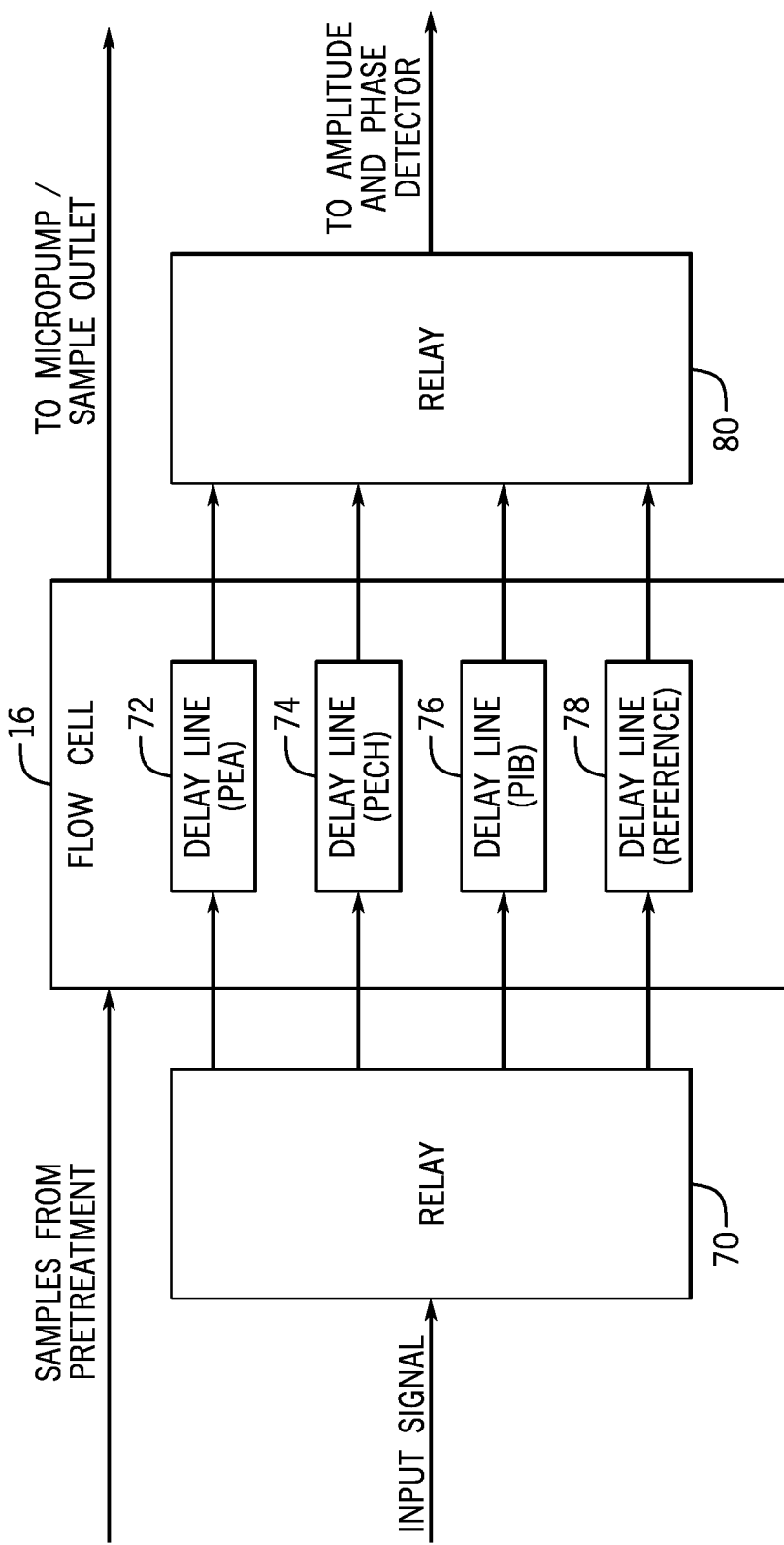
FIG. 3 is a schematic diagram of an exemplary embodiment of a flow cell for use with the sensor system of FIG. 1.
Figure 4:
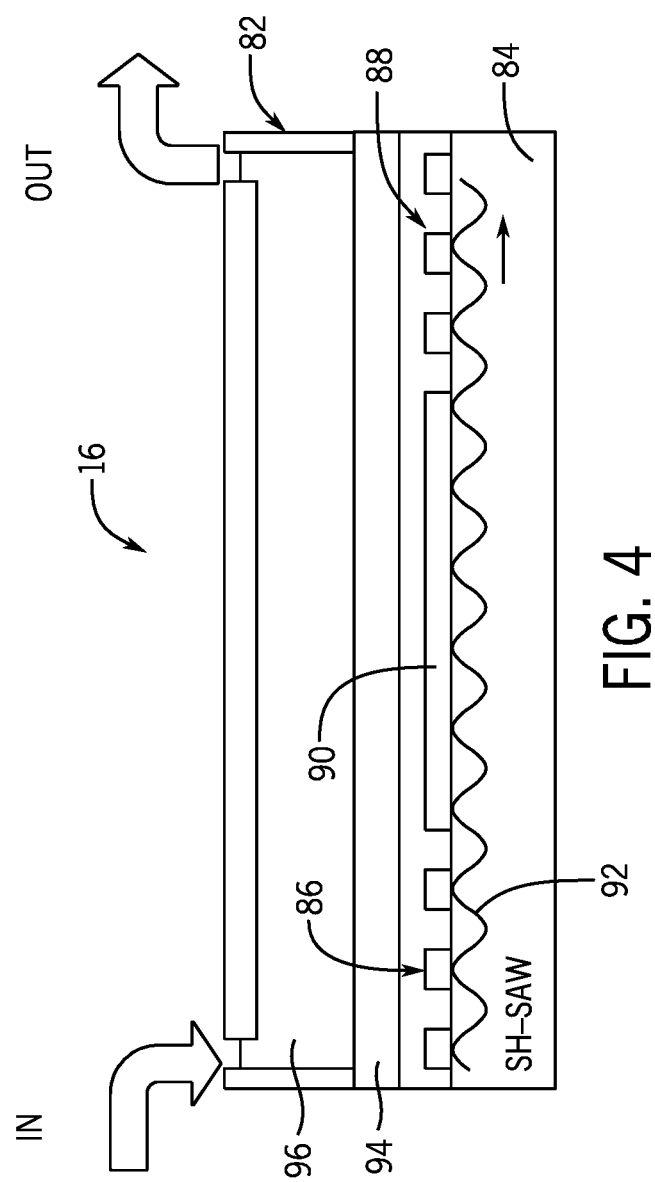
FIG. 4 is a cross-sectional view of an exemplary embodiment of a flow cell and a delay line.

In a still further exemplary embodiment, the pretreatment stage 12 may further include a pre-concentration unit designed to concentrate the hydrocarbons in the test sample for detection by the flow cell. In an exemplary embodiment, the pre-concentrator may be that disclosed in U.S. Pat. No. 9,244,051 entitled Detection of Hydrocarbons in Aqueous Environments, which is incorporated by reference herein in its entirety. Such a pre-concentrator may be located in various locations within the pretreatment stage 12. Two such locations being prior to the particle filter 40 and after the ion exchange filter 58, for example parallel to the reference water supply 60 to pre-concentrate the test sample "B". In the latter case, the reference sample "A" could either be provided as described above, or the sample from the ion exchange filter 58 could be used as the reference sample "A" without further treatment. It will be recognized that these locations are exemplary and not limiting with respect to implementations of the disclosure provided herein. Embodiments as described herein without a pre-concentrator enable the detection of benzene at exemplarily concentrations less than 100 ppb (parts per billion), less than 50 ppb, and/or greater than 10 ppb. Embodiments using a pre-concentrator as described above may achieve a 10× increase in BTEX analyte concentration, which may increase the sensitivity of such a sensor embodiment to detect concentrations of benzene less than 10 ppb and/or greater than 1 ppb FIG. 3 is a schematic diagram of an exemplary embodiment of a flow cell 16 as may be used in connection with the sensor system 10 depicted in FIG. 1. FIG. 4 is an exemplary cross-sectional view through the flow cell and a delay line. The flow cell 16 selectively receives the reference and test samples from the pretreatment stage 12 as described with respect to FIG. 2. The received sample (test or reference) flows across the flow cell 16 which includes a plurality of delay lines which are embodied in SH-SAW sensors. The reference and test samples are directed out of the flow cell 16 to the micro-pump 18 and the sample outlet 20 as depicted in FIG. 1.

In an exemplary embodiment, an input relay 70 receives the input signal exemplarily from the power splitter 30 (FIG. 1) and selectively applies the input signal to each of a plurality of delay lines one at a time in order to prevent cross talk between the delay lines. As will be described in further detail herein, other arrangements and configurations may be used to provide the input signal to the delay lines.

Figure 10:
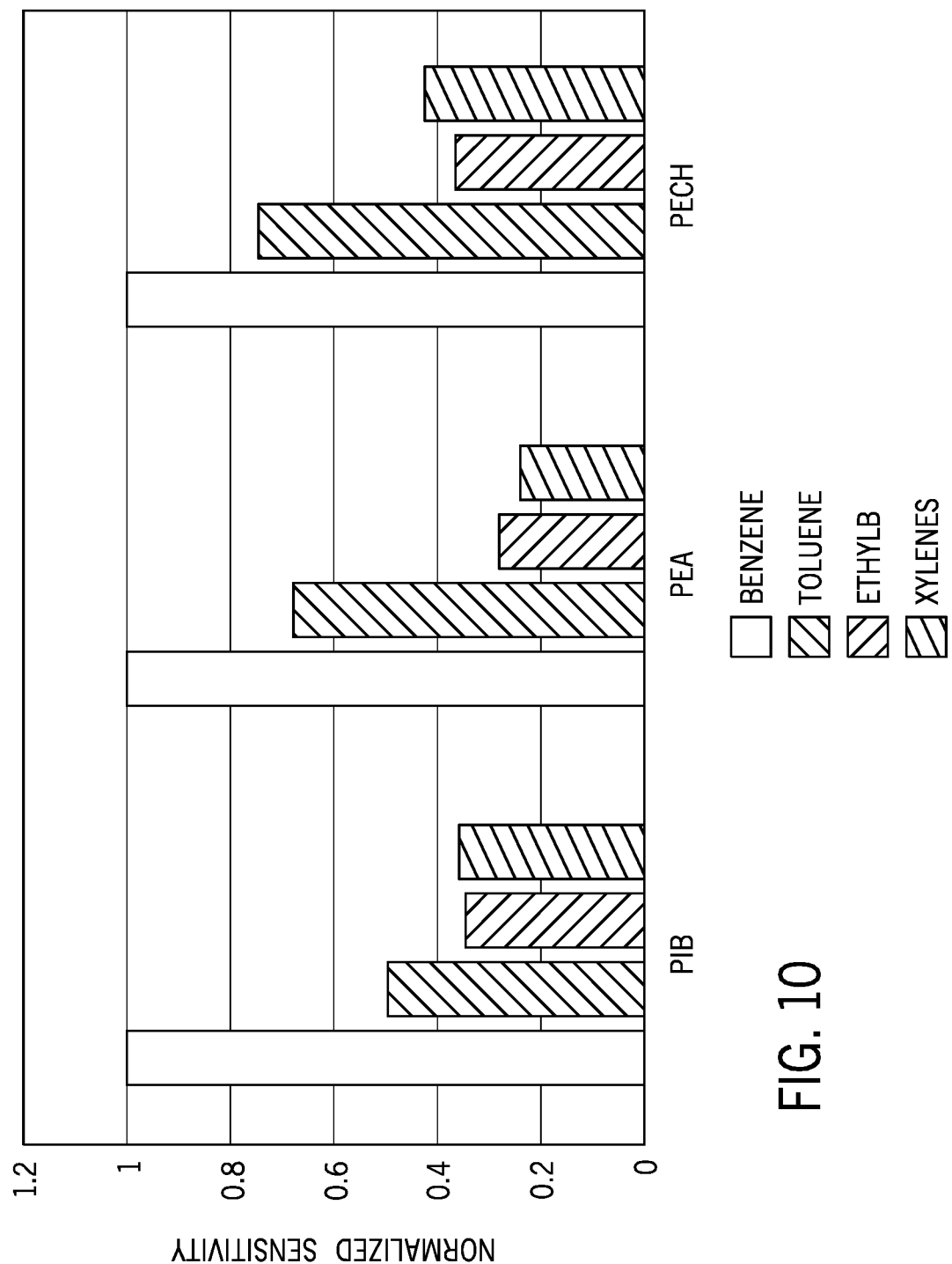
FIG. 10 is a graph that depicts normalized sensitivity of PIB, PEA, and PECH coatings to BTEX compounds.

The flow cell 16 includes a plurality of delay lines, each delay line treated with a different sorbent polymer coating. The different polymer coatings are selected to interact with the analytes of interest (e.g. BTEX). The exemplary embodiment of the flow cell 16 depicted in FIG. 3 includes four delay lines. Delay line 72 is exemplarily coated with poly (ethyl acrylate) (PEA). Delay line 74 is exemplarily coated with poly(epichlorohydrin) (PECH). Delay line 76 is exemplarily coated with poly(isobutylene) (PIB). Each of these polymer coatings are exemplarily e.g. available from Sigma-Aldrich, St. Louis, Mo. Delay line 78 is a reference delay line and is exemplarily coated with poly(methyl methacrylate) (PMMA) (e.g. available from Scientific Polymer Products, Ontario, N.Y.). The PMMA polymer coating of the delay line 78 is exemplarily baked for 120 minutes at 180° C., resulting in a glassy, non-sorbent coating so that the reference line does not absorb appreciable amounts of analyte (i.e. it is chemically insensitive) at the concentrations and time scales of interest. FIG. 10 presents graphs of normalized sensitivity to the BTEX analytes by each of the sorbent polymer coatings described above (PEA, PECH, PIB).

In addition to the above commercially available polymers, sensor coatings based on polymer-plasticizer blends can also be used. Examples include PS-DIOA (polystyrene-diisooctyl azelate), which can be used with a mixing ratio of about 17 to 23% w/w DIOA in PS depending on the application and preferred coating characteristics (such as sensitivity and partial selectivity to a given analyte, and long-term stability), and PS-DINCH (polystyrene-diisononyl cyclohexane-1,2-dicarboxylate), which can be used with a mixing ratio of about 21 to 25% w/w DINCH in PS.

The delay line 82 (FIG. 4) is constructed of a substrate 84. The substrate 84 is exemplarily constructed of 36° rotated YX—LiTaO$_3$. It will be recognized that other materials of configurations, including but not limited to Langasite or quartz may potentially be used. Exemplary embodiments of delay lines which may be used in embodiments are described in further detail in Bender et al., Anal. Chem., Vol. 86, 2014: pp 11464-11471, which is incorporated herein by reference in its entirety. The transducers are positioned on the substrate; exemplarily, two identical interdigital transducers (IDT) may be used for each delay line 82. The delay line 82 includes a transmitter IDT 86 and a receiver IDT 88 which are separated by a metalized surface region 90. The metalized surface region 90 eliminates acoustoelectric interactions within the region between the transmitter IDT 86 and the receiver IDT 88. The metalized surface region 90 helps to limit unwanted electrical coupling between the SH-SAW and the fluid in the flow cell. In embodiments, the transmitter IDT 86 and the receiver IDT 88 are identical multi-electrode IDTs. In an exemplary embodiment the IDTs include a plurality of electrode fingers each with a width of 5 micrometers and a gap between adjacent electrode fingers of 5 micrometers. In exemplary embodiments of multi-electrode IDTs, the IDTs may exemplarily include four electrode fingers per electrical period or 12 electrode fingers per electrical period, although a person of ordinary skill in the art will recognize that other IDT designs may be used within the scope of the present disclosure. It will further be recognized that the sensor may include equal numbers of fingers of each polarity per period, or may be unbalanced in the number of fingers with each polarity. The periodicity of the IDT ($P_{IDT}$) is based upon the pattern of electrodes in the IDT. An operational frequency of the IDT which is embodied in the input signal described above provided to each of the delay lines may be selected based upon the periodicity of the IDT sensor. In an exemplary embodiment, the delay line 82 is configured to hold optimal use with a shear horizontal-surface acoustic wave 92 produced by a transmitter IDT 86 at a frequency of 102 megahertz. This is exemplarily the third harmonic of the IDTs with 12 electrode fingers per electrical period mentioned above, or the fundamental SH-SAW frequency for the IDT with four electrode fingers per electrical period. It will be recognized that other input signal frequencies may be suitable in other embodiments, based upon the design of the IDTs. In embodiments, the input signal may be selected to have a frequency equal to a fundamental frequency or harmonic frequency of the IDT.

As described above, the IDT is covered with a sorbent polymer coating 94. The sorbent polymers of PEA, PECH, and PIB were all selected to exhibit different sorption characteristics and thus different patterns of sensitivity of a sensor with that coating to the various BTEX analytes as will be described in greater detail herein. The polymer coating also acts as an acoustic waveguide for the SH-SAW 92. In use, the liquid samples 96 will move across the polymer coating 94 and the BTEX analytes are selectively absorbed by each respective polymer coating according to the sorption characteristic of the polymer coating. This sorbs the analytes from the liquid of the sample for interaction with the SH-SAW 92, causing a frequency and/or amplitude shift in the signal obtained at the receiver IDT 88 as compared to the input signal applied to the transmitter IDT 86.

In embodiments, the sensor system, and more particularly the flow cell 16 may operate in three operational conditions. These operational conditions may be controlled by the microcontroller 34 selectively operating the valves, micropumps, and relays of the system. First, the pretreatment system 12 is operated to provide the reference sample "A" to the flow cell until the flow cell reaches a steady state or equilibrium response to the reference sample. Then the pretreatment system is operated to provide the test sample "B" containing the analytes to be tested to the flow cell. For example, this is achieved by operating the valve 66 by the micro controller 34. The sensor responses to the test sample are measured. After the measurements are obtained (and the analyte concentrations determined), the pretreatment system (e.g. valve 66) is operated again to introduce the reference sample to the flow cell to flush the flow cell of any remaining analyte. This may further be combined with a purge condition, for example, by operation of valve 68 and micropump 50 by the microcontroller to connect the air inlet 48 through the flow cell. Further description of this operation may be exemplarily found in Bender et al., Joint Conference of the IEEE International Frequency Control & the European Frequency & Time Form, 2011, or in Bender et al., Anal. Chem. Vol. 86, 2014: pp 1794-1799, or Bender et al., Joint UFFC, EFTF and PFM Symposium, 2013 which are all incorporated herein by reference in their entireties.

Referring back to FIG. 3, in one embodiment a relay 80 is connected to each of the delay lines 72-78 to similarly receive the electrical output from each of the delay lines and provide the output for signal processing, for example with an amplitude and phase detector and/or microcontroller.

Figure 5:
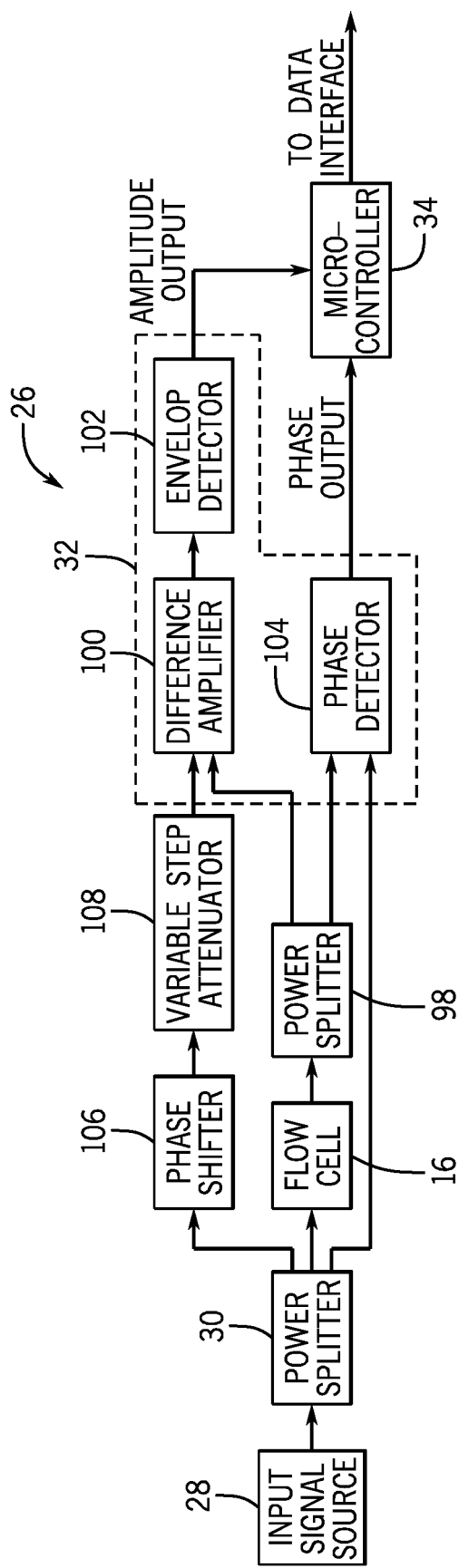
FIG. 5 is a schematic block diagram of an exemplary embodiment of a sensor measurement system for use with the sensor system of FIG. 1.

FIG. 5 is a schematic block diagram of an exemplary embodiment of a sensor measurement system 26 for use with the sensor system of FIG. 1. The sensor measurement system 26 includes the input signal source 28, and the power splitter 30, both of which have been previously described above with respect to FIG. 1. In an exemplary embodiment, the input signal source 28 provides a 102 megahertz signal to the power splitter 30. In an exemplary embodiment, the power splitter 30 may be a three-way 0° power splitter which provides the input signal to the flow cell 16 as well as to separate amplitude and phase detection systems. In an alternative embodiment, the signal amplitude and phase detector 32 may be used which may only require a single input signal. In an embodiment, the phase detector detects a phase shift that correlates to a frequency shift used by the microcontroller to determine the analyte concentrations as described herein, while in another embodiment, a frequency shift may be measured directly with a frequency detector, although it has been observed that in some embodiments the phase detection may produce more accurate frequency shift results when making an aqueous phase measurement.

As described above, the power splitter 30 provides the input signal to the relay 70 of the flow cell 16 (FIG. 3). The relay operates to sequentially provide the input signal to each of the delay lines to prevent cross talk between the delay lines. In an alternative embodiment, the relay 70 may be removed and instead an additional power splitter (not depicted) may be added to the sensor measurement system 26 and the input signal may be continuously provided to all of the delay lines in the flow cell 16.

Whether the flow cell sequentially provides the input signal to each of the delay lines or each of the delay lines are continuously powered with the input signal, the output signal of the flow cell 16 is provided to a power splitter 98 which is exemplarily a two-way 0° power splitter. In an embodiment wherein all of the delay lines simultaneously produce an output signal, it will be recognized that multiple power splitters 98 and amplitude and phase detectors 32 may be used and/or may include multiple channels for use. The power splitter 98 exemplarily provides the output signals to the amplitude and phase detector 32. The amplitude and phase detector 32 exemplarily includes a difference amplifier 100 and an envelope detector 102 that are used to process the output signal to produce an amplitude output. The amplitude and phase detector 32 further includes a phase detector 104 that receives the output from the power splitter 98 to produce a phase output. The amplitude output and the phase output are provided to a microcontroller as described in further detail herein for further signal processing.

In an exemplary embodiment of the sensor measurement system 26 as depicted in FIG. 5, the power splitter 30 further provides the input signal to both the phase detector 104 as well as to the difference amplifier 100, after signal processing. Such signal processing may include a phase shifter 106 and a variable step attenuator 108 such that the processed input signal may be used as a reference signal to the difference amplifier 100 for detection of the amplitude shift across the flow cell 16. Similarly, the input signal provided by the power splitter 30 to the phase detector 104 acts as a reference for detection of the phase shift and the output of the flow cell 16. In an alternative embodiment, rather than recording each of the responses of the output signals from each of the delay lines, the output of the reference delay line may be used as the reference signal for calculating of differential amplitude shift and phase shift between the reference output and each of the delay line outputs. In such an embodiment, the input signal need not be provided as a reference to the amplitude and phase detectors 32, but rather the output of the reference delay line would be provided to the amplitude and phase detector 32.

Figure 6:
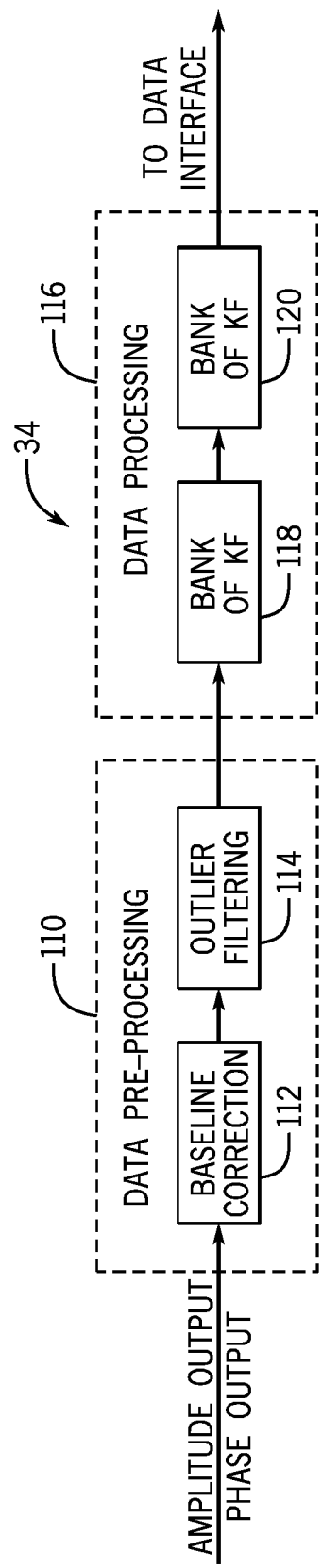
FIG. 6 is a schematic block diagram of the data processing exemplarily performed by the microcontroller of the sensor system of FIG. 1.

FIG. 6 is a schematic block diagram of the data processing exemplarily performed by the microcontroller 34 of the sensor system 10 of FIG. 1. The microcontroller 34 exemplarily stores measured sensor signal at a local data storage unit 36. The microcontroller 34 further exemplarily contains computer readable code embodying software stored on computer readable memory therein. Upon execution of the computer readable code by the microcontroller, the microcontroller carries out the data processing as described in further detail herein. The microcontroller 34 exemplarily processes the amplitude outputs and phase outputs from the sensor measurement system as described above in respect to FIG. 5. In embodiments, the microcontroller may either receive a frequency shift from a frequency shift detector, may receive the phase shift outputs and determine corresponding frequency shifts from the phase shift outputs, or may receive frequency shifts as already determined from the phase shifts detected by the phase detector.

The microcontroller 34 carries out data pre-processing 110. The data pre-processing 110 exemplarily removes or minimizes signal drifts and outliers remaining in the log data and corrects for the reference line response exemplarily caused by local temperature variation, transient changes in pressure, or other changes in environmental condition. The output of the reference delay line provides a reference for these corrections. At 112 a baseline correction is exemplarily subtracting any linear baseline drift remaining in the difference between the sensor line output and the reference line output. At 114 outlier filtering is performed to correct any outliers in the data above a certain threshold to account for transient disturbances (e.g. pressure spikes) which may affect the data. While not depicted in FIG. 6, the data pre-processing 110 may further include a monitoring system which provides an alert for reaching an end of life for each sensor for example by comparing the output amplitude for each sensor to a threshold value and indicating if the output amplitude becomes too low which indicates that the attenuation across that delay line has become too high.

At 116 the data processing to identify and quantify BTEX compound is performed with bank of Kalman filters as will be described in greater detail herein. The design of the data processing and banks of Kalman filters is based upon estimation theory and reliance upon both response time and steady-state sensitivity for each combination of BTEX analytes and the polymer coating of the delay line sensor. This will be explained in greater detail further herein. It will be recognized that in embodiments Kalman filters (KFs) or extended Kalman filters (EKFs) may be used based upon the linearity of the underlying sensor response models. An extended Kalman filter is a special case of Kalman filter adapted for use with non-linear models. Therefore, Kalman filters may be used in embodiments as described herein, but in an embodiment where the sensor response models are non-linear the Kalman filters may be extended Kalman filters.

In an exemplary embodiment, multiple banks of Kalman filters are used to carry out the data processing. A first bank of Kalman filters 118 is used to obtain a rough estimate of the concentration of the BTEX compounds in the measured sample. The second bank of Kalman filters 120 is used to refine the estimate of the concentration of the BTEX compounds provided by the first bank of Kalman filters to produce a final estimate of BTEX compound concentrations. The output of the microprocessor 34 is provided to the data interface 38 for transmission to be used or monitored on a computer system. As noted above, if the sensor response models are linear, then the first bank and second bank may comprise Kalman filters, while if the sensor response models are non-linear, then the first bank and the second bank may comprise extended Kalman filters.

In an alternative embodiment the first bank of Kalman filters may be replaced with a recursive least squares technique. In such an embodiment, the recursive least squares technique is used to narrow down the expected ranges of concentration for each of the analytes to produce a rough estimate (within the narrow concentration ranges) of the concentration of each of the BTEX compounds. As explained in greater detail herein, the recursive least squares technique may be used with linear sensor response models, thus the recursive least squares technique may be used in combination with a bank of Kalman filters. In such an embodiment, the bank of Kalman filters 120 is used for the same purpose of refining a received estimate of the concentration of the BTEX compounds to produce the final estimate of BTEX compound concentrations.

As mentioned above, the presently disclosed solution detects and quantifies BTEX compounds in an aqueous solution in the presence of interferents by implementing a method based upon estimation theory. In order to implement estimation theory, it is necessary to analytically model the sensor response. Thus in order to model the SH-SAW sensor response to aqueous mixtures of multiple BTEX compounds, the sensor responses to individual analytes had to be characterized.

The response to a step change in analyte concentration in the 0-10 ppm range is well modeled using a single exponential fit, as represented in Equation 1.

$$\Delta f(t) = \Delta f_o \left[ 1 - e^{-\frac{t}{\tau}} \right], \quad (1)$$

where $\Delta f_o$ is the equilibrium frequency shift, $\tau$ is the response time constant, and $\Delta f(t)$ is the frequency shift as a function of time.

Fitting a sensor response to Equation 1 yields a characteristic value of $\tau$ for each combination of polymer coating and BTEX analyte. Experimental results show $\tau$ to be independent of analyte concentration in the range of interest and, for a given sensor coating, it therefore can be used to identify the analyte. The single-analyte experiments also provide sensitivities (Hz of frequency shift per ppm-by-mass of analyte concentration) for each combination of sensor coating and BTEX compound, which, like the response times, are independent of concentration (and hence the equilibrium frequency shifts can be conveniently used to determine analyte concentration(s)). As chemical isomers, ethylbenzene and the three xylenes are found to have nearly identical values for their response times and sensitivities; therefore, no attempt was made to distinguish between them. The average values of response time constants and sensitivities for various coating/analyte combinations are listed in Tables 1 and 2.

TABLE 1

Measured Mean Response Times, τ (in s), for Three Different Polymer Coatings to Various BTEX Analytes, Together with their Standard Errors (n = 5)

| Polymer | $\tau_{benzene}$ | $\tau_{toluene}$ | $\tau_{ethylbenzene}$ |
| --- | --- | --- | --- |
| 1.0 μm PEA | 36.1 (±10.0) | 76.7 (±6.0) | 204 (±4.5) |
| 0.6 μm PECH | 26.5 (±8.4) | 77.6 (±2.8) | 175 (±13) |
| 0.8 μm PIB | 29.3 (±7.8) | 84.2 (±6.5) | 245 (±14) |

TABLE 2

Measured Mean Sensitivities, σ (in Hz/ppm), for Three Different Polymer Coatings to Various BTEX Analytes, Together with their Standard Errors (n = 5)

| Polymer | $\sigma_{benzene}$ | $\sigma_{toluene}$ | $\sigma_{ethylbenzene}$ |
| --- | --- | --- | --- |
| 1.0 μm PEA | 244 (±27) | 690 (±160) | 2240 (±460) |
| 0.6 μm PECH | 109 (±9) | 435 (±25) | 1450 (±240) |
| 0.8 μm PIB | 63 (±5) | 344 (±43) | 1670 (±10) |

In order to analytically model the sensor responses to single-analyte samples of BTEX compounds, an assumption was made that the responses obey Henry's law. Usually, when the sensor is exposed to a step change in the ambient concentration of an analyte, the sensor responds rapidly at first with the rate of change of the signal changing more slowly as the coating and analyte approach equilibrium. The process of analyte absorption for the case of a single-analyte sample can be fit by a first-order model described by Equations 2a and 2b.

$$\dot{C}(t) = -\frac{1}{\tau}C(t) + \frac{K_{p-w}}{\tau}C_{amb}(t) \quad (2a)$$

$$\Delta f(t) = -aC(t), \quad (2b)$$

where C(t) is the concentration of analyte in the coating at time t, $C_{amb}(t)$ is the ambient analyte concentration at time t (which for these experiments remains constant for t>0 due to the constant flow of fresh analyte solution throughout the measurement), τ is the response time constant for a given analyte/coating combination, $K_{p-w}$ is the polymer/water partition coefficient for a given analyte/coating pair, Δf(t) is the frequency shift observed at time t, and a is the steady-state or equilibrium sensitivity, which is a function of the sensor platform, the sensor coating, and the analyte.

Equation 2b represents the measured SH-SAW device frequency shift for the single-analyte system at time t. Solving the differential Equation 2a yields an exponential time dependence with response time constant τ, which, when substituted into Equation 2b, yields a single exponential expression in the form of Equation 1, with $\Delta f_0 = aC(\infty)$.

Next, the single-analyte sensor response must be extended to multi-analyte responses. Sensor responses to binary analyte mixtures are well modeled by dual exponential fits and the total equilibrium frequency shift in response to a binary mixture is the sum of the frequency shifts for the individual analytes (i.e., $\Delta f = \Delta f_1 + \Delta f_2$). The sensor response for the binary mixture can be modeled using a dual-exponential fit which can be expanded to a sensor response to a mixture containing n analytes that can be modelled using n exponential terms as given by Equation 3.

$$\Delta f(t) = \Delta f_1\left[1 - e^{-\frac{t}{\tau_1}}\right] + \Delta f_2\left[1 - e^{-\frac{t}{\tau_2}}\right] + \ldots + \Delta f_n\left[1 - e^{-\frac{t}{\tau_n}}\right] \quad (3)$$

where $\Delta f_i$ and τ are the equilibrium frequency shift and the response time constant, respectively, associated with the $i^{th}$ analyte. If the sensitivities of each analyte in the mixture are known, the concentration of each analyte in the mixture can be extracted.

The generic analytical model for the sensor response to a mixture of n analytes can be obtained by making two major assumptions: first, as noted above, it is assumed that the mixture obeys Henry's law. From this assumption, it can be inferred that for a dilute mixture of multiple soluble species, the sorption of any given species into the polymer does not affect the sorption of the other species in any way. Free partitioning of analytes between polymer and aqueous phase is inferred, including the implication that the sorption process is fully reversible at ambient temperature (i.e. only physisorption occurs). Based on experimental observations, Henry's law is valid for analyte concentrations in the range of 0 to at least 10 ppm depending on the analyte. Moreover, Henry's law implies that the concentration of the mixture in the coating at any time t is simply the sum of the concentrations of the individual analytes: $C_{mixture}(t) = C_1(t) + C_2(t) + \ldots + C_n(t)$ for any time t, where $C_i(t)$ represents the concentration of each analyte in the mixture as it would be measured in a single-analyte response. The process of analyte absorption can then be assumed to be first order (similar to the model of single-analyte sensor response). The second assumption is that the equilibrium frequency shifts are also mutually independent: the frequency shift due to the mixture at any time t is the sum of the frequency shifts due to each analyte in the mixture at that time. Based on these two assumptions, the sensor response to a mixture of the n analytes can be represented by Equations 5a and 5b.

$$\dot{C}_i(t) = -\frac{1}{\tau_i}C_i(t) + \frac{K_{p-w,i}}{\tau_i}C_{amb,i}(t) \quad (5a)$$

and $$\Delta f(t) = -\sum_{i=1}^{n} a_i C_i(t), \quad (5b)$$

where all the variables are as previously defined, with subscript i=1, 2, . . . , n referring to each analyte in the mixture.

In order to use the generic model of Equations 5a and 5b to detect and quantify target analytes in the presence of interferents, the following assumptions are made: first, that there can be an unknown number of interferents present together with the target analytes; second, that the sensor response(s) due to these interferents does not dominate the response(s) due to the target analytes. From experimental observations for BTEX in groundwater (as described further below), we find that the interferents either have slower response time constants or lower sensitivities than the four target analytes. In other applications, this condition often can be met by using appropriate sorbent coatings, e.g. coatings with significantly larger partition coefficients for the analytes than interferents. When the selected coatings and the set of interferents are such that the time-dependent absorption for all the interferents is relatively similar, a simple approach is to represent their combined response by a single exponential term. In such cases, Equations 5a and 5b can be used to represent the sensor response of n−1 target analytes (i=1, 2, . . . , n−1) and the collection of interferents (i=n).

From experiments with the polymer coatings listed above and several of the interferents found in oil and fuel (as reported in further detail herein), their contributions to the sensor response indeed do not dominate those of the BTEX compounds, and/or these interferents are found to have response time constants significantly longer than those of the BTEX compounds. The fact that ethylbenzene and the three xylenes are chemical isomers means that, in applying Equations 5a and 5b, their combined response can be represented by a single exponential term. Thus, the subscripts i=1, 2, 3 represent the target analytes benzene, toluene, and the combination of the four C8 isomers, respectively, and the subscript i=4 represents the combined response due to the interferents in the mixture and the BTEX compounds. Thus, in embodiments, polymer coatings are selected that produce a strong (i.e. sensitive) response to BTEX. In embodiments, the polymer coatings are further selected such that other interferents exhibit a weak and/or slow response.

The models explained above were used to develop the estimation-based theory approach for the detection and quantification of BTEX compounds in the presence of interferents. For that purpose, the sensor response model of the multi-analyte mixture of Equations 5a and 5b were normalized, discretized, and converted into state-space form. Equations 5a and 5b were normalized by dividing by $K_{p-w,i} C_{max,i}$ (where $C_{max,i}$ represents the equilibrium ambient concentration). By defining new variables as:

$$m_i(t) = \frac{C_i(t)}{K_{p-w,i} C_{max,i}}, \quad (6a)$$

$$u_i(t) = \frac{C_{amb,i}(t)}{C_{max,i}}, \quad (6b)$$

and $$\alpha_i = -a_i K_{p-w,i} C_{max,i}, \quad (6c)$$

the following normalized equations are obtained:

$$\dot{m}_i(t) = -\frac{1}{\tau_i} m_i(t) + \frac{1}{\tau_i} u_i(t) \quad (7a)$$

and $$\Delta f(t) = \sum_{i=1}^{4} \alpha_i m_i(t), \quad (7b)$$

where, for analyte i, $m_i(t)$ represents the normalized concentration absorbed at time t, $\alpha_i$ is the equilibrium frequency shift, and $u_i(t)$ represents the step in concentration for the transition from clean water to the sample (for t<0, $C_{amb,i}(t)=0$; for t>0, $C_{amb,i}(t)=C_{max}$).

Because sensor data are collected at discrete-time instants (i.e. $t=kT_s$, where $T_s$ is the sampling period and k is a non-negative integer), it is necessary to transform the continuous time-normalized model of the sensor response of Equations 7a and 7b into a discrete-time model. Using Euler's first-order forward method, Equations 7a and 7b become:

$$m_{i,k}+(1-S_i)m_{i,k}+S_i u_{i,k}+v_k \quad (8a)$$

and $$\Delta f_k = \sum_{i=1}^{4} \alpha_i m_{i,k} + w_k, \quad (8b)$$

where $S_i$ is the absorption rate constant $$\left(\text{i.e. } S_i = \frac{T_s}{\tau_i}\right).$$

The terms $v_k$ and $w_k$ are added to represent the process and measurement noise, respectively, which are likely to be present in the system. It is assumed that both process and measurement noise are white noise (uncorrelated in time) and also that they are uncorrelated with each other.

The unknown parameters that need to be estimated in the model defined by Equations 8a and 8b for successful quantification of BTEX compounds in the presence of interferents include the equilibrium frequency shifts (i.e. $a_i$, i=1,2, 3,4), the absorption rate constant of the fourth analyte (i.e. $S_4$), and the normalized concentration of the fourth analyte (i.e. $m_{4,k}$). Note that the normalized concentration is related to the absorption rate constant. In order to facilitate the estimation process, Equations 8a and 8b are converted into state-space form by assigning state variables to the unknown parameters:

$$\begin{bmatrix} x_k^{(1)} \\ x_k^{(2)} \\ x_k^{(3)} \\ x_k^{(4)} \\ x_k^{(5)} \\ x_k^{(6)} \end{bmatrix} = \begin{bmatrix} S_4 \\ m_{4,k} \\ \alpha_1 \\ \alpha_2 \\ \alpha_3 \\ \alpha_4 \end{bmatrix} \quad (9)$$

and the resulting discrete-time state-space form is as follows:

$$x_{k+1} = f(x_k, u_k, v_k) = \begin{bmatrix} x_{k+1}^{(1)} \\ x_{k+1}^{(2)} \\ x_{k+1}^{(3)} \\ x_{k+1}^{(4)} \\ x_{k+1}^{(5)} \\ x_{k+1}^{(6)} \end{bmatrix} = \begin{bmatrix} x_k^{(1)} \\ (1 - x_k^{(1)})x_k^{(2)} + x_k^{(1)} u_{1,k} + v_k \\ x_k^{(3)} \\ x_k^{(4)} \\ x_k^{(5)} \\ x_k^{(6)} \end{bmatrix} \quad (10a)$$

and $$y_k = h(x_k, u_k, w_k) = x_k^{(3)} m_{1,k} + x_k^{(4)} m_{2,k} + x_k^{(5)} m_{3,k} + x_k^{(6)} x_k^{(2)} + w_k. \quad (10b)$$

Equation 10b is specifically referred to as the output equation. From Equations 10a and 10b, it can be seen that the state-space representation is a nonlinear model. Therefore, a nonlinear estimator has to be used to estimate the unknown parameters; the state estimates are denoted as $\hat{x}_k$. It will be recognized that while a non-linear model may be used if the sensor system is to be implemented using two banks of EKFs, in an embodiment wherein the recursive least squares technique is used with a bank of EKFs, then a linear model is used to estimate the unknown parameters during the recursive least squares technique.

Discrete-time extended Kalman filtering (EKF) was used to estimate the unknown parameters, requiring the nonlinear system to be linearized using a Taylor series expansion about the current state estimate, $\hat{x}_k$. The result of linearization and the generalized expressions of the terms are used to define the following EKF algorithm:

$$\hat{x}_{k+1} = \quad (11a)$$
$$f(\hat{x}_k, u_k, \bar{v}) + A_k P_k C_k^T (C_k P_k C_k^T + G_k W_k G_k^T)^{-1}[y_k - h(\hat{x}_k, u_k, \bar{w})]$$

and $$P_{k+1} = \quad (11b)$$
$$A_k P_k A_k^T + F_k V_k F_k^T - A_k P_k C_k^T (C_k P_k C_k^T + G_k W_k G_k^T)^{-1} C_k P_k A_k^T,$$

where $$A_k = \begin{bmatrix} 1 & 0 & 0 & 0 & 0 & 0 \\ -\hat{x}_k^{(2)} + u_{B,k} & (1-\hat{x}_k^{(1)}) & 0 & 0 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{bmatrix},$$

$$F = \begin{bmatrix} 0 \\ 1 \\ 0 \\ 0 \\ 0 \\ 0 \end{bmatrix},$$

$$C_k = [\,0 \quad \hat{x}_k^{(6)} \quad m_{1,k} \quad m_{2,k} \quad m_{3,k} \quad \hat{x}_k^{(2)}\,],$$

and $$G = [1].$$

In Equation 11, the term $P_k$ represents the error covariance matrix and $(\bullet)^T$ denotes a matrix transpose. This EKF algorithm can be applied to perform the estimation of the unknown parameters, which, in turn, allows for the quantification of the detected analytes of interest.

The above EKF algorithm starts with an initial estimate of the state vector, $\hat{x}_0$ (i.e. the state variables) and the error covariance matrix, $P_0$. The initialization of the state vector, $\hat{x}_0$, requires initializing the unknown parameters in Equation 9. Based upon an initial estimate of the state vector, $\hat{x}_0$, the initial error covariance, $P_0$ is set. If the initial value of the state vector, $\hat{x}_0$, is completely unknown, an educated guess is made and a value set for the initial state estimate, $\hat{x}_0$, and the initial error covariance, $P_0$, is set to a large value. After each measurement of a new data point, the state estimates and error covariance are updated based on this acquired information. The update process is repeated recursively until the unknown parameters converge to a particular value. Using this algorithm, the equilibrium frequency shift for each detected BTEX compound can be estimated, enabling the concentrations of the detected BTEX compounds to be extracted by dividing the estimated equilibrium frequency shift of each BTEX compound by its corresponding average sensitivity. The above EKF algorithm can be implemented by a microcontroller or readily available software packages. Supporting information on the actual derivation of the EKF equations is available.

As described above, the microcontroller employs at least one bank of Kalman filters (KFs or EKFs), while in an exemplary embodiment employs at least two banks of Kalman filters, to identify and quantify BTEX analytes in the water samples. Alternatively, the microcontroller uses a recursive least squares technique to provide the initial estimate and a bank of Kalman filters to refine the initial estimate to a final estimate of analyte concentrators. Using the discrete-time state-space models found in Equations 10 and 11 with measured frequency shifts as a function of response time from each coated sensor for the water samples collected at a series of discrete-time instants (i.e. at each sampling period), the estimation of the unknown parameters (BTEX concentrations vs. time) was performed using EKF. Since the state-space model is highly nonlinear (it includes bilinear terms), a bank of several EKFs with different initial estimates was used to estimate the six states of the system in order to obtain more accurate results. The working principle of a bank of EKFs is very similar to that of a single EKF, except that the sensor response is processed simultaneously by several EKF estimators in parallel, each using different initial conditions, and the estimates from the filter are combined in order to generate the final estimates of the states at each instant of time.

In the exemplary embodiment described above with respect to FIG. 6, initial conditions of the KF or EKF in the first bank of Kalman filters may be based upon likely concentration ranges of individual BTEX compounds that could be expected to be present in the water sample, for example in the 10 to 2000 ppb range. The corresponding range of equilibrium frequency shifts for each BTEX compound was determined by multiplying the concentration range by the average sensitivity for the respective BTEX compound. The range of equilibrium frequency shifts was then used to initialize all the filters in the bank. The estimates obtained from all the KFs or EKFs are combined using weights, which are updated recursively using each KF or EKF's estimate of the error covariance in the measurement as well as its estimate of the measurement. The filters that produce the smallest error covariance are given the most weight. In order to combine the estimates from all the filters, the weight of each filter is multiplied by its corresponding estimate, and the resulting products are added to produce an average estimate of the unknown parameters.

Embodiments as disclosed herein estimate the time constant of the responses from the sensors. The analyte concentrating can be accurately estimated once the time can be reliably determined. Thus, well before the sensor reaches a steady state or a response to other interferents is detectable, the time constant of the sensor response can be determined and analyte concentration accurately estimated. In embodiments this may be achieved in 4-7 minutes.

These estimates of the unknown parameters are then used as the initial conditions of the KFs or EKFs in the second bank of Kalman filters which similarly process the data to arrive at refined estimates of the unknown parameters, namely the concentrations of the individual BTEX compounds in the water sample.

Figure 7:
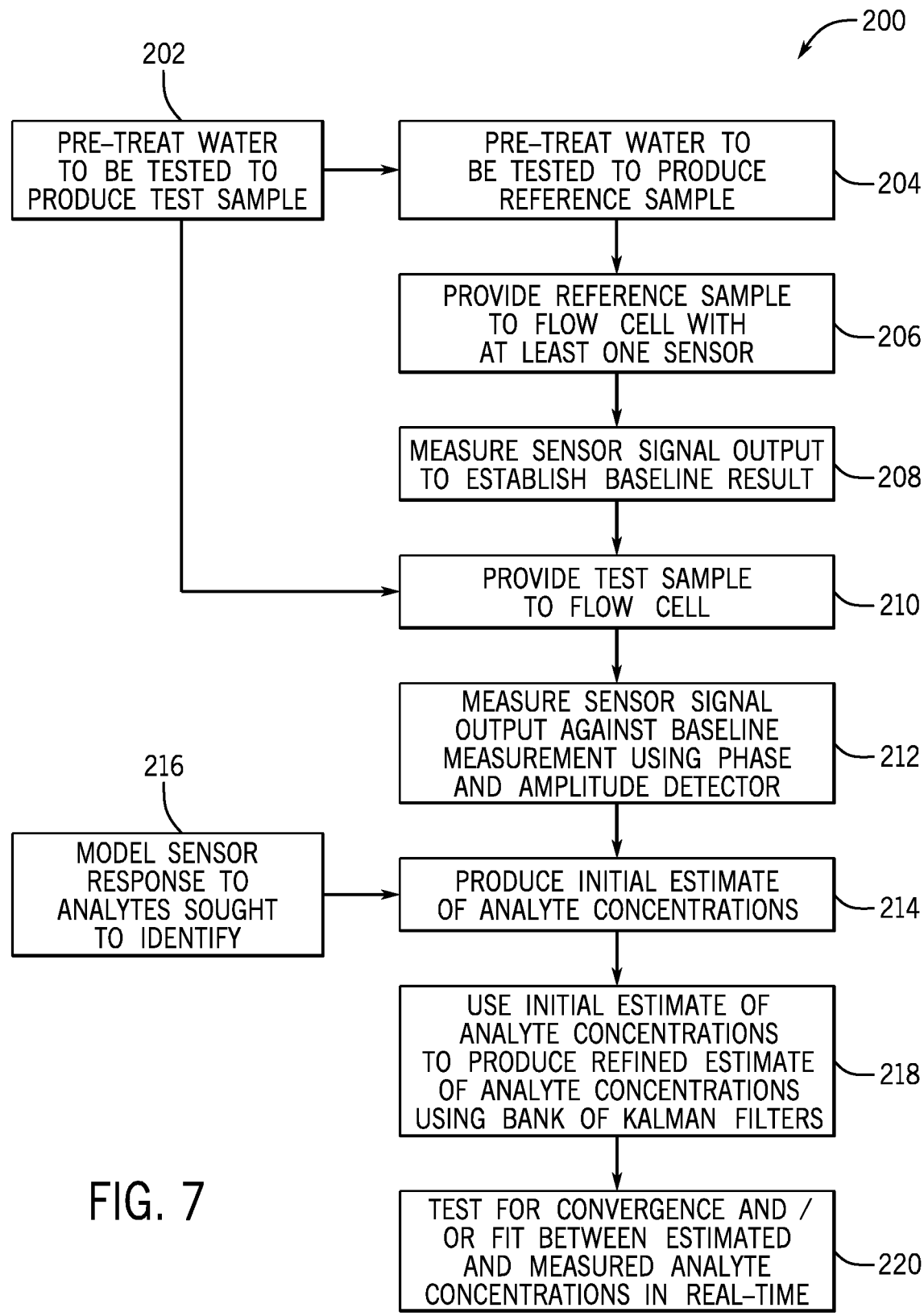
FIG. 7 is a flow chart that depicts an exemplary embodiment of a method of detecting hydrocarbons in an aqueous solution.

FIG. 7 is a flow chart that depicts an exemplary embodiment of a method 200 of detecting hydrocarbons in an aqueous solution. The method 200 begins at step 202 when a water sample to be tested is pretreated to produce a test sample. The pretreatment of the water may be performed as described previously in the present application may include particle filtering, removal of gas bubbles, and processing through an ion exchange filter. Optionally at 204, the water to be tested may be further pretreated to produce a reference sample. This further pretreating at 204 may include pretreating that is specifically designed to remove hydrocarbons from the sample of water to be tested. This may exemplarily be formed by degasification or with a charcoal filter, although other technique may be used and recognized. In an embodiment in which the reference sample does not come from further pretreating of the water to be tested, an independent reference sample may be provided in the method.

At 206 the reference sample is provided to a flow cell that includes at least one sensor. In an exemplary embodiment, the at least one sensor is an SH-SAW sensor with a selectively absorbent polymer coating and the flow cell direct the flow of the reference sample through the flow cell across the at least one sensor. In exemplary embodiments the flow cell comprises multiple sensors, each of these sensors having a different polymer coating. At 208, a signal from the at least one sensor is measured to establish baseline result. In an exemplary embodiment, the at least one sensor is provided with an input signal and the output from the at least one sensor exhibit at least one of an amplitude change and a frequency shift based upon the conditions sensed by the sensor. The baseline result obtained in the presence of the reference sample can account for the unremoved interference remaining in the water to be tested apart from the hydrocarbon analytes sought to be identified and quantified in other conditions of the sensor, including, but not limited to ambient temperature and wear on the sensors, particularly in the polymer coating of the sensors.

At 210 the test sample is provided to the flow cell. Test sample is exemplarily provided as a step wise change or discontinuity of input compared to the reference sample. For example, this is controlled by a three way valve that selectively provides either the reference sample to the flow cell or the test sample to the flow cell.

At 212 the sensor's signal output is measured against the baseline measurement to produce a differential measurement of the phase shift and amplitude change relative to the baseline results. This may be performed using a phase and amplitude detector as previously described.

The differential phase shift and amplitude changes are exemplarily provided to a micro controller which at 214 produces an initial estimate of the analyte concentrations in the test sample. To do this, at 216 the responses of the sensors in the flow cell to the analytes sought to be identified are previously modeled and provided to the microcontroller. The sensor responses may be mathematically modeled from underlying laboratory testing measurements techniques for modeling these sensor responses are previously described above. The microcontroller uses the modeled sensor responses to produce the initial estimate of analyte concentrations at 214 for example using a recursive least squares technique, a bank of Kalman filters, or a bank of extended Kalman filters (depending upon the linearity or non-linearity of the sensor response models) to solve for each analytes' contribution to the received output signal.

At 218 the initial estimate of the analyte concentration from 214 are used to produce a refined estimate of the analyte concentrations using a bank of Kalman filters. Thus, in one embodiment, two banks of Kalman filters may be used, while in another embodiment a bank of Kalman filters is used only to produce the refined estimate of analyte concentration.

Finally, at 220 the estimates of analyte concentration are tested for goodness of fit and/or convergence conditions for estimate of analyte concentrations in real-time. Thus, while in embodiments once the refined estimate of analyte concentrations are produced at 218, the measurement may be completed, despite the sensors in the flow cell having not reached an equilibrium or steady state response to the test sample. However, if the sensor continues to obtain measurements, then the estimate of analyte concentrations may be further refined.

While not limiting on the scope of the embodiments as described in detail herein, exemplary embodiments of the sensor system as disclosed herein may be used in numerous applications and settings. The prominent, while not limiting, example, used in the present disclosure is that of groundwater monitoring, exemplarily at UST sites. This may include initial site assessment (e.g. plume delineation) and/or long-term monitoring to evaluate remediation performance or demonstrate monitored natural attenuation. Other applications may include wastewater and stormwater monitoring, clean up scenarios, monitoring oil plumes at sea, monitoring of hydrocarbon storage, handling, and transportation infrastructure/equipment (e.g. pipelines and tanks) for leak detection. While BTEX monitoring has been used as the primary example, other embodiments by be used to monitor organic compounds other than BTEX (although it will be noted that such embodiments may require changes to the selected polymer coatings on the sensors).

EXAMPLES

In order to test the validity of the formulated signal processing model, which accounts for chemical interferents, the coated sensors were exposed to four different compounds selected to represent the classes of interferents commonly encountered in groundwater at release sites. No significant response to ethanol was found up to concentrations of 100 ppm. For MTBE, a very low sensitivity was found (~1 Hz/ppm). Since this compound is usually present at low concentrations, its effect on the sensor response can also be neglected. For 1,2,4-trimethylbenzene and n-heptane, high sensitivities (>1 kHz/ppm) and long response times were found. The high sensitivities indicate that, normally, these compounds cannot be ignored even at the low concentrations commonly encountered. However, since their response times are longer than those of the BTEX compounds, they can be conveniently modeled by the last (i=4) term in eq 8b. The same is expected to hold true for other larger aromatic or aliphatic compounds.

The sensor and signal processing approach described in the present application were validated by conducting a large number of measurements of responses to BTEX-containing samples by an embodiment of the disclosed SH-SAW sensor. The concentration results were measured using the disclosed bank of EKFs as described. Two representative estimation results are presented here in detail to illustrate the overall process.

Figure 8:
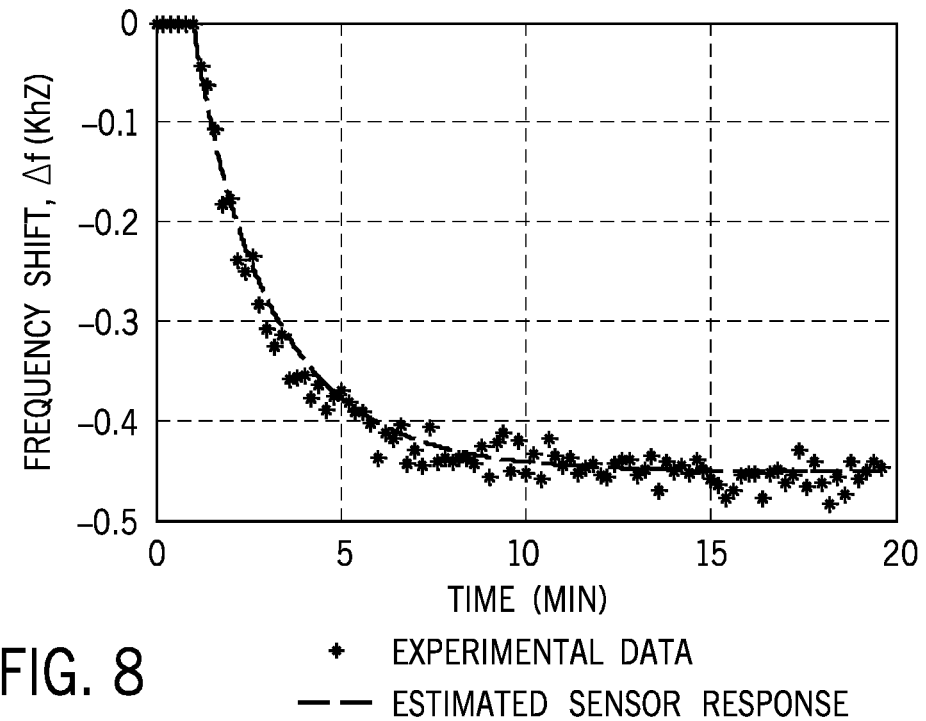
FIG. 8 is a graph depicting an exemplary sensor response and an estimated sensor response.

FIG. 8 and Table 3 present such results for an exemplary embodiment of a sensor system coated with 0.6 μm PECH to a light non-aqueous phase liquid (LNAPL) sample (in groundwater) including 197 ppb of benzene, 241 ppb of toluene, and 16 ppb of ethylbenzene and xylenes in the presence of typical interferents (as indicated by gas chromatograph-photoionization detector (GC-PID) and gas chromatograph-mass spectrometer (GC-MS)). FIG. 1 shows excellent agreement between the measured data points and the estimation, calculated by substituting the estimated equilibrium frequency shifts and corresponding time constants into Equation 4 (with n=4). Note that this estimation technique allows the unknown parameters to be calculated well before the sensor response reaches equilibrium. In practice, it is found that the time for quantification has to be longer than the response times of all BTEX compounds (see Table 1). Using the sensitivities of BTEX compounds (Table 2), their concentrations are extracted by dividing the estimated equilibrium frequency shift for each compound by its corresponding average sensitivity. As summarized in Table 3, the estimated concentrations of BTEX compounds are in very good agreement with the actual concentrations: less than 15% difference on average. The actual concentration of BTEX compounds refers to measurements using a portable GC-PID. Table 3 also shows that the percentage difference between the actual and estimated concentrations of ethylbenzene and xylenes (EX) is relatively high compared to those of benzene and toluene, but the absolute difference is just 3 ppb, which is lower than the estimated detection limit for this analyte/coating combination (about 10 ppb). It is to be expected that in this low concentration range, the signal noise will limit the accuracy of the concentration estimation.

FIG. 8 depicts a measured response of a SH-SAW sensor coated with 0.6 μm PECH to a LNAPL sample in groundwater containing 197 ppb of benzene, 241 ppb of toluene, 16 ppb of ethylbenzene and xylenes, and an unknown number and concentration of interferents. FIG. 8 also depicts an estimated sensor response curve plotted using the estimated sensor parameters. The analysis as described above enables the single sensor response (or single responses of multiple sensors e.g. as depicted in FIG. 8) to be deconvolved into concentration estimates of the component analytes whose summed contribution (along with the contribution of any interferents) resulted in the sensor response.

Table 3 presents estimated concentrations of BTEX compounds obtained using measurement data of a LNAPL sample in groundwater as exemplarily collected using a SH-SAW sensor coated with 0.6 μm PECH and compared to actual BTEX compound concentrations in the sample

TABLE 3

| Analyte of Interest | Concentrations (ppb) | | % Difference |
|---|---|---|---|
| | Actual | Estimated | |
| Benzene | 197 | 219 | 11 |
| Toluene | 241 | 220 | 9 |
| Ethylbenzene & Xylenes | 16 | 19 | 19 |

Figure 9:
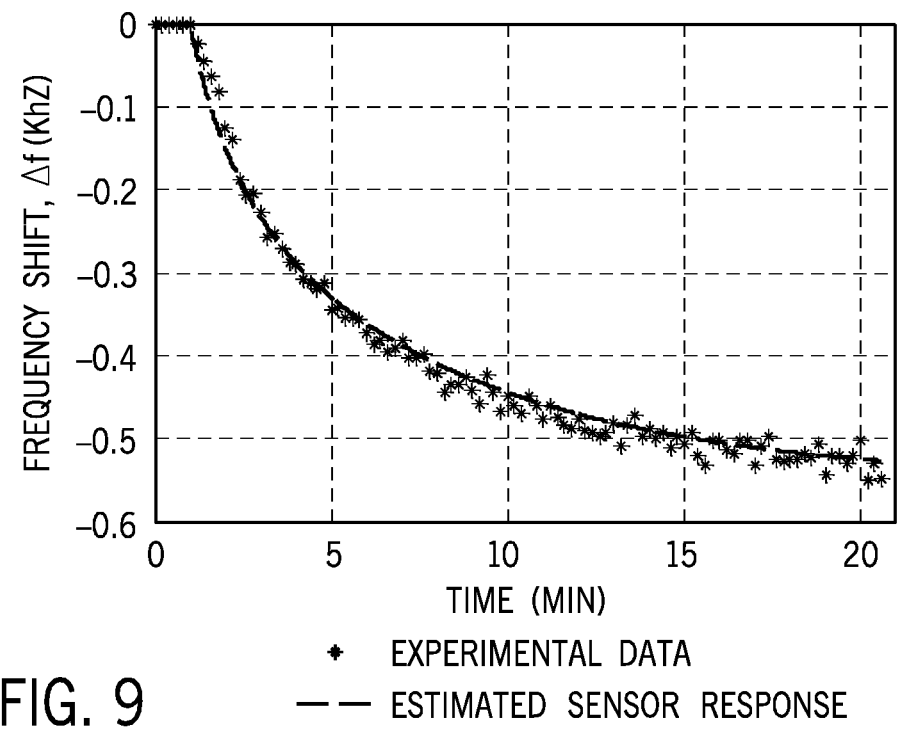
FIG. 9 is a graph depicting an exemplary sensor response and an estimated sensor response.

FIG. 9 and Table 4 show another estimated result obtained using the response of an exemplary embodiment of a sensing system, in this case coated with 0.8 μm PIB, to a LNAPL sample (in DI water) including 610 ppb of benzene, 874 ppb of toluene, and 154 ppb of ethylbenzene and xylenes, and various interferents present in LNAPL. In FIG. 9, the estimated sensor response curve shows excellent agreement with the measured data points, hence the estimated equilibrium frequency shifts should be close to the actual values. The equilibrium frequency shifts are then used to extract the concentrations of BTEX compounds; the results, listed in Table 4, are in very good agreement with the actual concentration values (less than 5% difference on average). Better agreement is not expected due to the error (5-10%) of the GC-PID instrument used to measure the absolute concentrations. For this example, the estimation method enabled the BTEX analytes to be quantified in less than half the time required for the sensor response to reach equilibrium.

FIG. 9 depicts a measured response of a SH-SAW sensor coated with 0.8 μm PIB to a LNAPL sample in DI water containing 610 ppb of benzene, 874 ppb of toluene, 154 ppb of ethylbenzene and xylenes, and various interferents. FIG. 9 also depicts an estimated sensor response curve plotted using the estimated sensor parameters.

Table 4 presents estimated concentrations of BTEX compounds obtained using measurement data of a LNAPL Sample in DI water as exemplarily collected using a SH-SAW sensor coated with 0.8 μm PIE and compared to actual BTEX compound concentrations in the sample

TABLE 4

| Analyte of Interest | Concentrations (ppb) | | % Difference |
|---|---|---|---|
| | Actual | Estimated | |
| Benzene | 610 | 597 | 2 |
| Toluene | 874 | 919 | 5 |
| Ethylbenzene & Xylenes | 150 | 154 | 3 |

As demonstrated in the above examples, each polymer coating exhibits a different analyte response. This difference between the analyte responses to each of the coatings, together with the different response time constants for different BTEX compounds, enables the system to discriminate between the chemically similar BTEX compounds. FIG. 10 presents the sensitivity of each of the three exemplary coatings (PIB, PEA, PECH) to each of the BTEX analytes. The sensitivity is normalized to the sensitivity of the coating to Benzene.

FIG. 10 depicts normalized sensitivities of three different polymer coatings (PIB, PEA, PECH) to the BTEX analytes. The exemplary coatings had the following thicknesses: 0.5 μm PIB, 0.6 μm PECH, 1.0 μm PEA. All analyte sample concentrations were 20 ppm.

As indicated above, a large number of measurements were made from multiple LNAPL samples diluted in groundwater or DI water, with BTEX concentrations ranging from low ppb to low ppm levels, and the estimation-based signal processing technique was applied. The results from these tests are summarized in FIG. 11, which includes estimates obtained using SH-SAW sensors coated with 0.6 μm PECH and 0.8 μm PIB. Most of the estimated concentration values in FIG. 11 lie quite close to the ideal line (slope of one), meaning that the estimates are in very good agreement with the actual concentrations in the various samples. The relative percentage errors between estimated and actual concentrations (relative to the actual concentration over all tested identical dilutions of a given sample) were calculated and are shown in the legend boxes of FIG. 11. Overall, the relative percentage error between the estimated and actual concentrations of BTEX compounds is less than 15%; for benzene, it is less than 10%.

Figure 11:
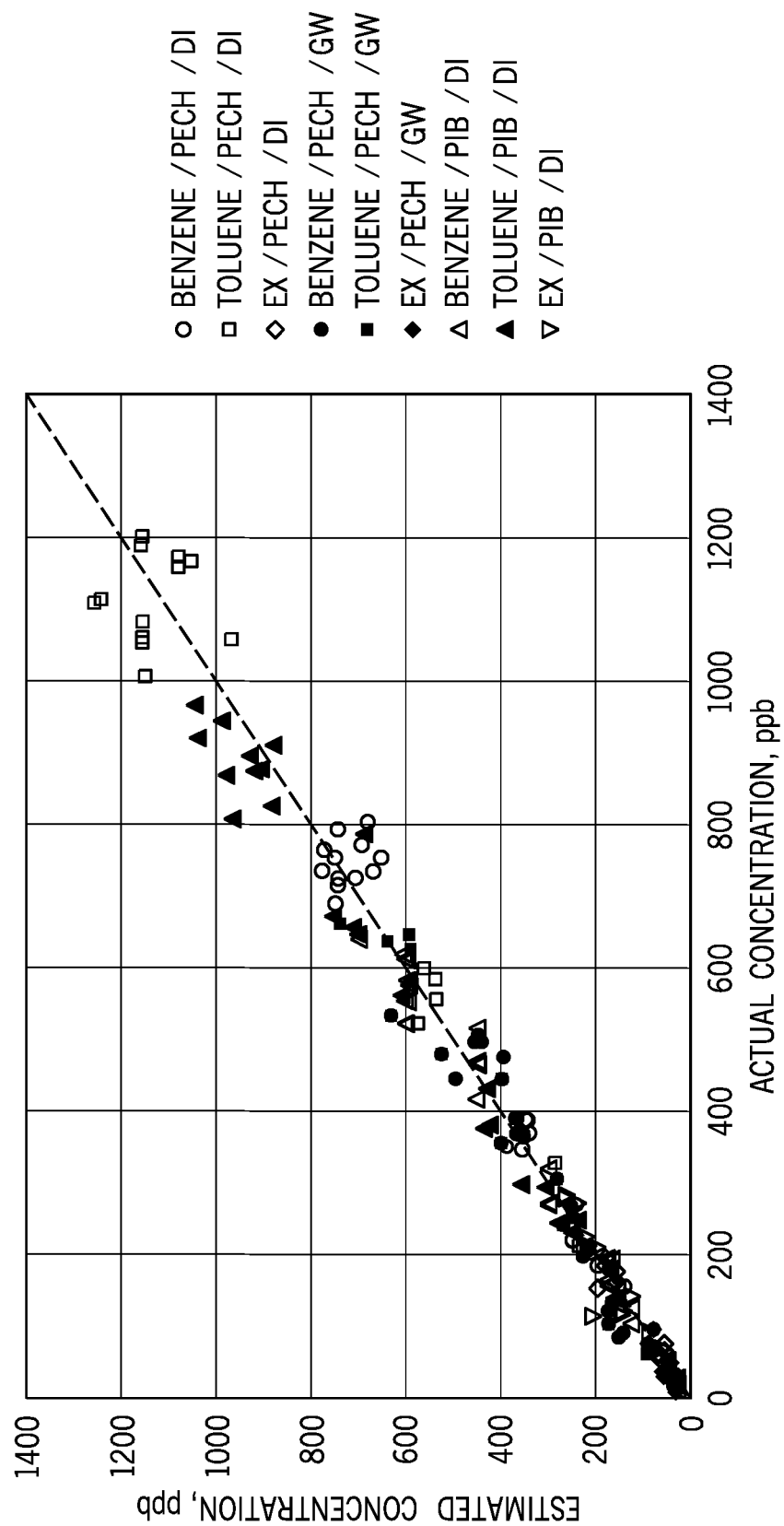
FIG. 11 is a graph presenting estimated versus actual concentrations of BTEX compounds.

The results summarized by FIG. 11 demonstrate the potential of estimation-based sensor signal processing to rapidly detect and quantify mixtures of BTEX compounds at ppb concentrations in the presence of interferents. This is realized using multiple sensing parameters, namely the characteristic time transients as well as equilibrium frequency shifts. This technique enables the use of a sensor array (not the traditional sensor array where the data from every sensors in the array must be processed together to achieve analyte recognition and quantification) with a small number of devices (2 to 3); choosing appropriate coatings provides identification redundancy and improved detection limits and accuracy, the last by averaging the results from all sensors in the array to yield an estimated value. From a single sensor response to a water sample containing a mixture of analytes, this technique is basically equivalent to a "deconvolution" process.

FIG. 11. Presents estimated versus actual concentrations of BTEX compounds in multiple LNAPL solutions in DI water obtained using estimated responses of a SH-SAW sensor coated with 0.6 μm PECH and 0.8 μm PIB. The dotted lines have a slope of one: the closer a point to the line, the more accurate the estimate.

While SH-SAW sensor arrays have previously been used to detect BTEX compounds in aqueous environments in the absence of interferents, for example in Bender et al., The 14$^{th}$ International Meeting on Chemical Sens., 2012, which is incorporated herein by reference in its entirety, embodiments as presently disclosed achieve significant progress in combining the responses of both time-transient and signal-amplitude data for each element of the array with estimation theory in order to detect and quantify BTEX compounds with greater reliability, improved chemical selectivity, even in the presence of interferents, higher quantitative accuracy, shorter time to collect the response data (using methods that do not require equilibrium to be attained before reporting a result), and shorter data processing time. In fact, we show for this application that estimation theory, particularly using a bank of Kalman filters (KF) or bank-of-extended-Kalman-filters (EKF) approach, allows analyte detection and quantification in near-real time. Importantly, this use of estimation theory is possible because the sensor responses can be modeled analytically: in the relevant concentration range.

The analytical capability of a sensor system has been investigated that combines polymer-coated SH-SAW sensor responses with signal processing using estimation theory for the purpose of detection and quantification of BTEX compounds in water in the presence of interferents. Based on experimental results, models for the sensor responses to single-analyte samples and mixtures of multiple analytes were developed, utilizing both the equilibrium frequency shifts and the response time constants. A state-space model for the quantification of BTEX compounds in the presence of interferents was formulated. Because embodiments of the model are nonlinear, a nonlinear estimator, specifically a bank of EKFs, was used to estimate the response parameters to these model embodiments. Embodiments of the model were tested using measured responses of polymer-coated SH-SAW sensors to LNAPL samples in water. Embodiments as disclosed herein were found to accurately quantify BTEX compounds in these samples, with most results falling within ±10% of the concentrations measured independently using a GC-PID. In particular, the estimated concentrations for benzene, toluene, and ethylbenzene-plus-xylenes fall within ±7%, ±10%, and ±14%, respectively, of the concentration from GC-PID measurements. These results indicate the ability of the formulated sensor signal processing method to tolerate the presence of interferents in the LNAPL samples in the quantification of BTEX compounds. A number of interferents present in the mixtures, i.e. n-heptane, 1,2,4-trimethylbenzene, MTBE, and ethanol were found not to affect the estimated results. These interferents, tested separately with the selected coatings and found to have low sensitivity and/or longer response times with the coatings, were accounted for in the model as a group. Concentrations of benzene in water down to 100 ppb were easily detected and quantified with the present system.

It is important to point out that the quantification of BTEX compounds in LNAPL solutions was performed in real-time as the data were collected. This was achieved with very good accuracy in less than half the time required for the sensor response to reach equilibrium. A major advantage of the signal-processing method demonstrated here is that it can be implemented using a microcontroller, which will enable the development of a small, portable, cost-effective sensor system for field use, including in confined spaces like groundwater monitoring wells. While the signal processing method was applied here to polymer-coated SH-SAW sensors, many other chemical sensor platforms could be used for a range of measurement applications and, in some scenarios, in the presence of interferents, provided the sensor responses can be modeled analytically. Possible alternative sensor platforms include MEMS-based sensors (e.g., microcantilevers), optical chemical sensors, chemiresistors, other types of acoustic wave-based sensors, and various solid-state devices. Finally, note that the proposed method also enables the use of a sensor array with a smaller number of devices (2 to 3 in this case), with appropriate coatings still necessary for redundancy, better accuracy by averaging, and improved detection limits.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description certain terms have been used for brevity, clarity, and understanding. No unnecessary limitations are to be inferred therefrom beyond the requirement of the prior art because such terms are used for descriptive purposes and are intended to be broadly construed. The different articles of manufacture and methods described herein above may be used alone or in combination with other articles of manufacture and methods.

The invention claimed is:

1. A system for sensing hydrocarbons in an aqueous solution, the system comprising:
   a pretreatment stage comprising a particulate filter, which receives the aqueous solution to be tested and operates to provide at least a test sample and a reference sample;
   a flow cell comprising at least one sensor with a polymer coating having at least partial selectivity for at least one analyte, the flow cell connected to the pretreatment stage and receives the test sample and the reference sample from the pretreatment stage; and
   a microcontroller that receives an output of the at least one sensor and executes computer readable code stored in a data storage device communicatively connected to the microcontroller, to process a frequency shift in the output of the at least one sensor with a bank of Kalman filters to estimate a concentration of at least one analyte in the aqueous solution.

2. The system of claim 1, wherein the at least one sensor comprises at least one SH-SAW sensor and the bank of Kalman filters comprises a bank of extended Kalman filters.

3. The system of claim 1, wherein the polymer coating is selected from poly(ethyl acrylate) (PEA), poly(epichlorohydrin) (PECH), poly(isobutylene) (PIB), polystyrene-diisooctyl azelate (PS-DIOA), and polystyrene-diisononyl cyclohexane-1,2-dicarboxylate (PS-DINCH).

4. The system of claim 1, wherein the at least one sensor comprises:
   a first delay line with a first SH-SAW sensor comprising a polymer coating of poly(ethyl acrylate) (PEA);

a second delay line with a second SH-SAW sensor comprising a polymer coating of poly(epichlorohydrin) (PECH);

a third delay line with a third SH-SAW sensor comprising a polymer coating of poly(isobutylene) (PIB); and a fourth delay line with a fourth SH-SAW sensor comprising a polymer coating of poly(methyl methacrylate) (PMMA).

5. The system of claim 4, wherein each of the first, second, third, and fourth delay lines receive an input signal and produce an output signal with an amplitude and a phase shift based upon the concentration of the hydrocarbons in the processed sample and the absorption of the hydrocarbons by the respective analyte selective polymer coatings and further comprising:

a phase detector that receives the output signals of from each of the first, second, third, and fourth delay lines and a phase reference signal, the phase detector outputs phase shifts for each of the output signals;

an amplitude detector that receives the output signals from each of the first, second, third, and fourth delay lines and an amplitude reference signal, the amplitude detector outputs differential amplitudes for each of the output signals;

wherein the microcontroller processes the phase shifts to determine corresponding frequency shifts for each of the output signals and processes the differential amplitudes to estimate the concentration of at least one analyte in the aqueous solution.

6. The system of claim 1, wherein the pretreatment stage further comprises a bubble trap operable to remove gas bubbles from the test sample.

7. The system of claim 6, wherein the pretreatment stage further operates to remove humic acid from the test sample.

8. The system of claim 7, wherein the pretreatment stage further comprises:

a hydrocarbon filter that receives the test sample and the output of the hydrocarbon filter is the reference sample; and a valve operable to selectively provide the test sample and the reference sample to the flow cell.

9. The system of claim 8, wherein the hydrocarbon filter comprises at least one of a degasser and a charcoal filter.

10. The system of claim 1, wherein the at least one sensor comprises:

a first delay line with a first SH-SAW sensor comprising a first polymer coating;

a second delay line with a second SH-SAW sensor comprising a second polymer coating;

a third delay line with a third SH-SAW sensor comprising a third polymer coating; and a fourth delay line with a fourth SH-SAW sensor comprising a fourth polymer coating;

wherein the fourth delay line is a reference delay line and the hydrocarbons consist of benzene, toluene, and ethylbenzene/xylenes;

wherein a phase detector receives the output signals of from each of the first, second, third, and fourth delay lines and a phase reference signal, the phase detector outputs phase shifts for each of the output signals;

wherein an amplitude detector receives the output signals from each of the first, second, third, and fourth delay lines and an amplitude reference signal, the amplitude detector outputs differential amplitudes for each of the output signals; and wherein the microcontroller processes the phase shifts to determine corresponding frequency shifts for each of the output signals and processes the differential amplitudes to estimate the concentration of at least one analyte in the aqueous solution.

11. A system for sensing hydrocarbons in an aqueous solution, the system comprising:

a pretreatment stage comprising a particulate filter, which receives the aqueous solution to be tested and operates provide at least a test sample;

a flow cell connected to the pretreatment stage and receives the test sample and a reference sample, the flow cell comprising:

a first delay line with a first SH-SAW sensor comprising a first polymer coating;

a second delay line with a second SH-SAW sensor comprising a second polymer coating;

a third delay line with a third SH-SAW sensor comprising a third polymer coating; and a fourth delay line with a fourth SH-SAW sensor comprising a fourth polymer coating, wherein the fourth delay line is a reference delay line and the hydrocarbons consist of benzene, toluene, and ethylbenzene/xylenes;

a phase detector receives the output signals of from each of the first, second, third, and fourth delay lines and a phase reference signal, the phase detector outputs phase shifts for each of the output signals;

an amplitude detector receives the output signals from each of the first, second, third, and fourth delay lines and an amplitude reference signal, the amplitude detector outputs differential amplitudes for each of the output signals; and a microcontroller that receives an output of the at least one sensor and executes computer readable code stored in a data storage device communicatively connected to the microcontroller, the microcontroller processes the phase shifts to determine corresponding frequency shifts for each of the output signals and processes the differential amplitudes to estimate the concentration of at least one analyte in the aqueous solution to process a frequency shift in the output of the at least one sensor with a bank of Kalman filters to simultaneously estimate a concentration of each of benzene, toluene, and ethylbenzene/xylenes in the aqueous solution.

12. The system of claim 11, wherein the bank of Kalman filters simultaneously processes the frequency shifts and the differential amplitudes from at least each of the first, second, and third delay lines.

13. The system of claim 12, wherein the bank of Kalman filters is a first bank of Kalman filters that produces an initial estimate of concentration of each of benzene, toluene, and ethylbenzene/xylenes in the aqueous solution, and further comprising a second bank of Kalman filters that use the first estimate as an initial condition and produce a refined estimate of a concentration of each of benzene, toluene, and ethylbenzene/xylenes in the aqueous solution.

14. The system of claim 11, wherein the microcontroller first processes the received differential amplitudes and frequency shifts with a recursive least squares technique that produces initial estimates of concentration of each of benzene, toluene, and ethylbenzene/xylenes in the aqueous solution, followed by the processing with the bank of Kalman filters using the initial estimates as initial conditions to produce refined estimates concentrations of each of benzene, toluene, and ethylbenzene/xylenes in the aqueous solution.

15. The system of claim 11, wherein the microcontroller produces the refined estimate of the concentration of each of benzene, toluene, and ethylbenzene/xylenes in the aqueous solution before a concentration of the hydrocarbons in the first, second, third, and fourth polymer coatings reaches a steady state.

16. The system of claim 1, wherein the pretreatment stage selectively provides the reference sample to the flow cell, and after the microcontroller detects a steady-state condition of the reference sample in the flow cell, the pretreatment stage selectively provides the test sample to the flow cell.

17. The system of claim 16, wherein after the microcontroller estimates the concentration of at least one analyte in the aqueous solution, the pretreatment stage selectively provides the reference sample to the flow cell.

18. The system of claim 17, wherein before the pretreatment stage provides the reference sample to the flow cell, the pretreatment stage purges the flow cell with a micropump connected to an air inlet.

19. The system of claim 1, further comprising a concentrator that operates to concentrate the hydrocarbons in the test sample.

* * * * *